(12) United States Patent
Marx

(10) Patent No.: US 8,246,589 B2
(45) Date of Patent: Aug. 21, 2012

(54) PRECISION LID RETRACTING EYEDROPPER DEVICE

(76) Inventor: Alvin J. Marx, San Antonio, TX (US)

( * ) Notice: Subject to any disclaimer, the term of this patent is extended or adjusted under 35 U.S.C. 154(b) by 572 days.

(21) Appl. No.: 12/319,908

(22) Filed: Jan. 12, 2009

(65) Prior Publication Data

US 2010/0022971 A1    Jan. 28, 2010

Related U.S. Application Data

(60) Provisional application No. 61/026,471, filed on Feb. 5, 2008, provisional application No. 61/075,768, filed on Jun. 26, 2008, provisional application No. 61/086,436, filed on Aug. 5, 2008, provisional application No. 61/097,153, filed on Sep. 15, 2008.

(51) Int. Cl.
*A61H 35/02* (2006.01)
*A61M 35/00* (2006.01)

(52) U.S. Cl. .......................... 604/302; 604/298

(58) Field of Classification Search ........... 604/294–303
See application file for complete search history.

(56) References Cited

U.S. PATENT DOCUMENTS

| | | | |
|---|---|---|---|
| 1,362,682 A * | 12/1920 | Dayton | 604/297 |
| 2,219,604 A * | 10/1940 | Trotter | 222/207 |
| 2,734,665 A * | 2/1956 | Flamm | 222/207 |
| 3,261,355 A * | 7/1966 | Burbig | 604/296 |
| 3,486,663 A * | 12/1969 | Humphrey | 222/207 |
| 3,872,866 A * | 3/1975 | Lelicoff | 604/302 |
| 3,934,590 A | 1/1976 | Campagna et al. | |
| 4,085,750 A * | 4/1978 | Bosshold | 604/302 |
| 4,111,200 A | 9/1978 | Sbarra et al. | |
| 4,115,042 A * | 9/1978 | Schroeder | 417/479 |
| 4,131,115 A * | 12/1978 | Peng | 604/297 |
| 4,336,895 A * | 6/1982 | Aleff | 222/207 |
| 4,349,133 A * | 9/1982 | Christine | 222/183 |
| 4,386,608 A * | 6/1983 | Ehrlich | 604/298 |
| 4,515,294 A * | 5/1985 | Udall | 222/105 |
| 4,543,096 A | 9/1985 | Keene | |
| 4,834,727 A * | 5/1989 | Cope | 604/300 |
| 4,927,062 A | 5/1990 | Walsh | |
| 4,973,322 A * | 11/1990 | Jewart | 604/300 |
| 4,981,479 A * | 1/1991 | Py | 604/302 |
| 5,040,706 A | 8/1991 | Davis et al. | |
| 5,064,420 A * | 11/1991 | Clarke et al. | 604/295 |
| 5,215,231 A * | 6/1993 | Paczonay | 222/610 |
| 5,261,571 A | 11/1993 | Goncalves | |
| 5,267,986 A * | 12/1993 | Py | 604/294 |
| 5,366,448 A * | 11/1994 | Basilice et al. | 604/290 |
| 5,370,267 A * | 12/1994 | Schroeder | 222/1 |
| 5,382,243 A * | 1/1995 | Mulholland | 604/301 |
| 5,401,259 A * | 3/1995 | Py | 604/294 |

(Continued)

*Primary Examiner* — Melanie Hand
*Assistant Examiner* — Paula Craig
(74) *Attorney, Agent, or Firm* — Kammer Browning PLLC

(57) ABSTRACT

Precision lid retracting eyedropper device with a hollow, rigid housing having an upper aperture that allows a push button topped piston to enter the housing where the piston can impinge on a resilient tubular member that is part of a pump assembly. The housing also includes a solution storing chamber that feeds solution to the pump assembly. A solution exit tube attached to the outgoing portion of the pump assembly emanates from the bottom part of the housing and can be directed towards the user's eye. Integral downwardly facing resilient legs are placed just above and below the user's orbital ridge so that when the legs are squeezed and released, the user's eye lids are forced open allowing the user to dispense a precise amount of solution into his or her eye.

5 Claims, 37 Drawing Sheets

U.S. PATENT DOCUMENTS

| | | |
|---|---|---|
| 5,516,008 A | 5/1996 | Rabenau et al. |
| 5,578,020 A | 11/1996 | Mosley |
| 5,611,464 A * | 3/1997 | Tsao et al. .............. 222/189.06 |
| 5,611,788 A * | 3/1997 | Marchment ................... 604/295 |
| 5,795,342 A * | 8/1998 | Shapiro et al. ............... 604/300 |
| 5,993,428 A * | 11/1999 | Hardge ......................... 604/294 |
| 6,010,488 A * | 1/2000 | Deas ............................. 604/295 |
| 6,090,086 A * | 7/2000 | Bolden ......................... 604/302 |
| RE37,047 E * | 2/2001 | Py ................................. 604/294 |
| 6,241,124 B1 | 6/2001 | Hoyt |
| 6,336,917 B1 * | 1/2002 | Berke ........................... 604/295 |
| 6,371,945 B1 | 4/2002 | Sherman |
| 6,595,970 B1 | 7/2003 | Davidian |
| 6,610,036 B2 * | 8/2003 | Branch et al. ................ 604/295 |
| 6,730,066 B1 | 5/2004 | Bennwik et al. |
| 6,736,802 B1 | 5/2004 | Recanati |
| 7,513,396 B2 * | 4/2009 | Pardes et al. ................. 222/494 |
| 7,621,273 B2 * | 11/2009 | Morton et al. ........... 128/205.23 |
| 2004/0039355 A1 * | 2/2004 | Gonzalez et al. ............ 604/298 |
| 2004/0111070 A1 * | 6/2004 | Hanley ........................ 604/295 |
| 2004/0173642 A1 * | 9/2004 | Clifford et al. .............. 222/420 |
| 2005/0131358 A1 * | 6/2005 | Skolik ........................ 604/295 |
| 2005/0147546 A1 * | 7/2005 | Long ....................... 422/186.07 |
| 2006/0079851 A1 * | 4/2006 | Guerrieri ..................... 604/295 |
| 2006/0264855 A1 * | 11/2006 | Goldenberg et al. ......... 604/294 |
| 2007/0055208 A1 * | 3/2007 | Berger et al. ................. 604/295 |
| 2007/0095862 A1 * | 5/2007 | Swiss et al. .................. 222/494 |
| 2009/0236374 A1 * | 9/2009 | Pardes et al. ................. 222/494 |
| 2009/0259204 A1 * | 10/2009 | Galdeti et al. ............... 604/302 |
| 2009/0293870 A1 * | 12/2009 | Brunnberg et al. ...... 128/203.12 |
| 2009/0318883 A1 * | 12/2009 | Sugahara et al. ............ 604/298 |
| 2010/0286633 A1 * | 11/2010 | Marx ........................... 604/296 |
| 2010/0286634 A1 * | 11/2010 | Marx ........................... 604/302 |

\* cited by examiner

PRECISION LID RETRACTING EYEDROPPER DEVICE

CROSS REFERENCE TO RELATED APPLICATIONS

This Application claims the benefit under Title 35 United States Code §119(e) of U.S. Provisional Application No. 61/026,471 filed Feb. 5, 2008; U.S. Provisional Application No. 61/075,768 filed Jun. 26, 2008, U.S. Provisional Application No. 61/086,436 filed Aug. 5, 2008, and U.S. Provisional Application No. 61/097,153 filed Sep. 15, 2008, the full disclosures of which are incorporated herein by reference.

BACKGROUND OF THE INVENTION

1. Field of the Invention

This invention relates generally to the field of solution dispensing devices and more specifically to a precision lid retracting eyedropper device.

2. Description of the Related Art

Devices for dispensing eye drop solutions are well known. Generally, a bottle of eye drop solution includes a drop dispenser that is either built into the exit orifice of the container, or is a separate drop applicator comprised of a tubular main body having a tapered exit aperture on one end and a rubber squeeze bulb on the opposite end. In the first instance, to dispense the solution, the user squeezes that bottle forcing solution out of the exit orifice and into his or her eye. In the second instance, the user squeezes and releases the rubber bulb causing solution to be drawn up into the applicator. The rubber bulb is then squeezed to force the solution into his or her eye. Many users have trouble with both types of dispensing systems. The user has a tenancy to blink when the drop is about to enter the eye, causing the drop to miss the eye and land on a closed lid.

Many of today's eye drop prescriptions call for precise dispensing of a specific amount of solution. Additionally, these prescription type solutions can be quite expensive, making any waste of solution quite costly. The precision needed for such applications can not be easily achieved with standard eyedropper devices. In addition, solution is wasted due to the user blinking during the application. Moreover, medication landing on the eyelid can cause skin irritation. Finally, eyedropper devices currently on the market do not have the ability to remain sterile after the first use. A clean and sterile eyedropper device would be preferable in many eye dropping applications.

A number of inventors have attempted to resolve the above mentioned problems. Thomas Keene, in his U.S. Pat. No. 4,543,096, discloses a dispenser with an eyelid opening device. The user is required to place a pair of lid spreading arms dangerously close to his eye and then to press a lever arm to keep the eyelids apart. No attempt is made to deliver a precise amount of solution. Thomas Sherman, in his U.S. Pat. No. 6,371,945, discloses an attachment for a bottle that includes a ring intended to help align the bottle with the eye. No attempt is made to hold the eyelid open or precisely meter the dose. Gary Campagna, in his U.S. Pat. No. 3,934,590, shows a tripod like device for aligning the solution bottle over the user's eye. No attempt is made to hold the lid open or to precisely measure the dose. James Davidian, in his U.S. Pat. No. 6,595,970, shows a device for dispensing eyed drops. He proposes a dispensing arm, one side of which includes an indentation that receives the user's nose, the other side of which accepts a dispensing bottle. The bottle includes a pair of arms which, when squeezed, impinge on the side walls of the bottle forcing solution out of the bottle and into the user's eye. No attempt is made to hold the user's eyelid open or precisely control the amount of fluid that exits from the bottle. James Walsh, in his U.S. Pat. No. 4,927,062, discloses a device that is intended to dispense a carefully measured amount of solution. However, no attempt is made to hold the device in the proper location or to hold the eyelid open. Manual Mosley's U.S. Pat. No. 5,578,020 shows a drop dispensing apparatus that attempts to control the amount of drops exiting from a bottle by pressing a deformable sleeve on the sides of the exit tube. No attempt is made to hold the eyelid open.

None of the above cited inventions dispenses a precise amount of eye drop solution and simultaneously holds the user's eyelids open while doing so. Additionally, none of the above cited inventions allows the eyedropper device to remain sterile after the first use.

SUMMARY OF THE INVENTION

The primary object of the invention is to provide a precision lid retracting eyedropper device that includes a means to hold the user's eyelids in an open position during the application of eyed eye drops.

Another object of the invention is to provide a precision eyedropper device that allows the user to release a precise and consistent amount of eye solution by pressing an easy release button.

Another object of the invention is to provide a precision eyedropper device that can remain sterile during multiple uses.

Another object of the invention is to provide a precision eyedropper device that allows the user to remove and replace a cartridge containing eye drop solution from a hollow housing.

A further object of the invention is to provide an alternate embodiment that allows the user to remove and replace a cartridge containing individual doses within individual chambers that can be removed and replaced from an eye drop dispensing device.

A further object of the invention is to provide a precision eyedropper device that is easy and economical to manufacture.

Other objects and advantages of the present invention will become apparent from the following descriptions, taken in connection with the accompanying drawings, wherein, by way of illustration and example, an embodiment of the present invention is disclosed.

In accordance with the first embodiment of the invention, there is disclosed a precision lid retracting eyedropper device comprising: a hollow, rigid housing that encloses a solution storage bladder, a solution pump assembly, a solution expelling piston and an exit port. The upper portion of the piston exits an aperture located in the top portion of the housing and terminates in a push button. When the piston presses on the pump resilient assembly it causes a repeatedly consistent amount of solution to be dispelled from the exit port. The housing includes a pair of integral downwardly disposed resilient legs that can be squeezed, then placed above and below the user's orbital ridge and then released causing the user's eyelids to be spread and to remain in the open position during the eye drop dispensing event.

In accordance with a second embodiment of the invention, there is disclosed a precision lid retracting eyedropper device comprising: a hollow, rigid, elongate cartridge body having a top cover and a bottom tubular aperture, that dispenses liquid, said cartridge capable of retaining a liquid solution, a cartridge holding housing having a hollow portion capable of retaining said removable cartridge, said cartridge housing including an aperture to allow the said tubular aperture of said cartridge to protrude out of the bottom of said housing, said cartridge housing including a pair of integral downwardly disposed resilient legs, said cartridge side wall having an aperture that is covered by a resilient membrane, and said cartridge including a inwardly biased check valve located in said top cover portion and an outwardly biased check valve mounted within said cartridge in front of said bottom dispensing aperture.

In accordance with a third embodiment of the invention, there is disclosed an eyedropper device comprising: a main body and a removable and replaceable eye drop cartridge. The cartridge includes individual eye drop containing ampoules. The eye drop solution is ejected from the resilient ampoule when a spring biased piston presses down on the ampoule causing a precise amount of solution to be ejected out into the user's eye whose eyelids have been held open by downwardly disposed flexible legs.

BRIEF DESCRIPTION OF THE DRAWINGS

The drawings constitute a part of this specification and include exemplary embodiments to the invention, which may be embodied in various forms. It is to be understood that in some instances various aspects of the invention may be shown exaggerated or enlarged to facilitate an understanding of the invention.

DETAILED DESCRIPTION OF THE PREFERRED EMBODIMENTS

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

Figure 1:
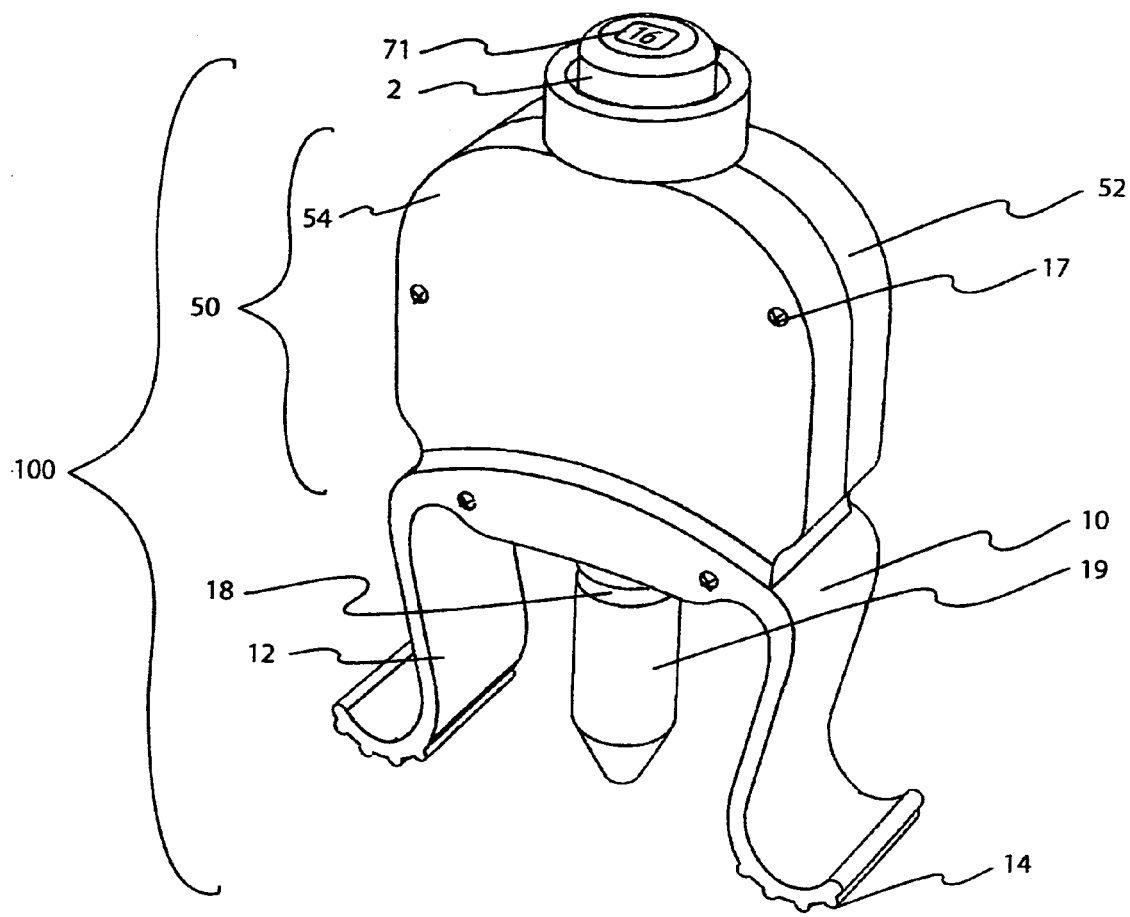
FIG. 1 is a perspective view of the first embodiment of the precision eye drop device of the present invention.

Referring now to FIG. 1 we see a front perspective view of the first embodiment of the precision eyedropper of the present invention 100. A hollow rigid housing 50 includes an integral resilient pair of downwardly facing legs 10, 12, that terminate in J shaped feet. Traction strips 14, located on the underside of each foot are designed to help stretch the user's orbital skin during operation as will be described below. The housing assembly 50 includes a back half 52 and a front half 54 held together by screws 17 or other standard fastening means.

Push button 2, when pushed, causes a precise amount of eye drop solution to be dispensed and will be described fully below. Push button 2 includes a standard counter 71 that advances one number after each use and will be described more fully below. Exit cover 19 protects the tip portion of the device 100 during storage. For ultimate sterility performance, a plurality of exit covers 19 can be included with the device 100 and a new cover 19 can be installed after each use. Inwardly facing detent 18 allows exit cover to be removable retained on the exit portion of the device 100.

Figure 2:
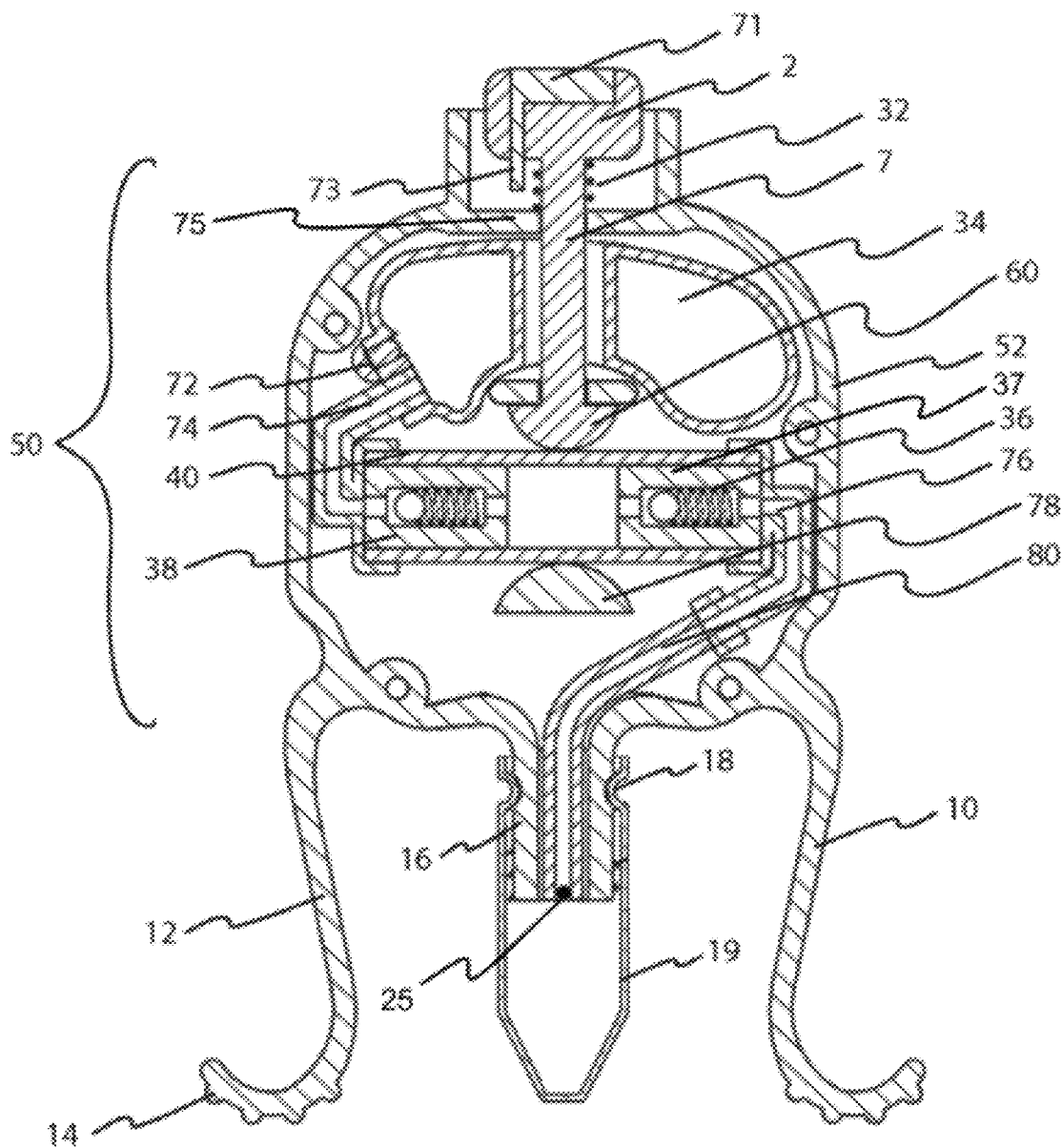
FIG. 2 is a front section view of the first embodiment of the eye drop device of the present invention with the storage cap in place.
Figure 9:
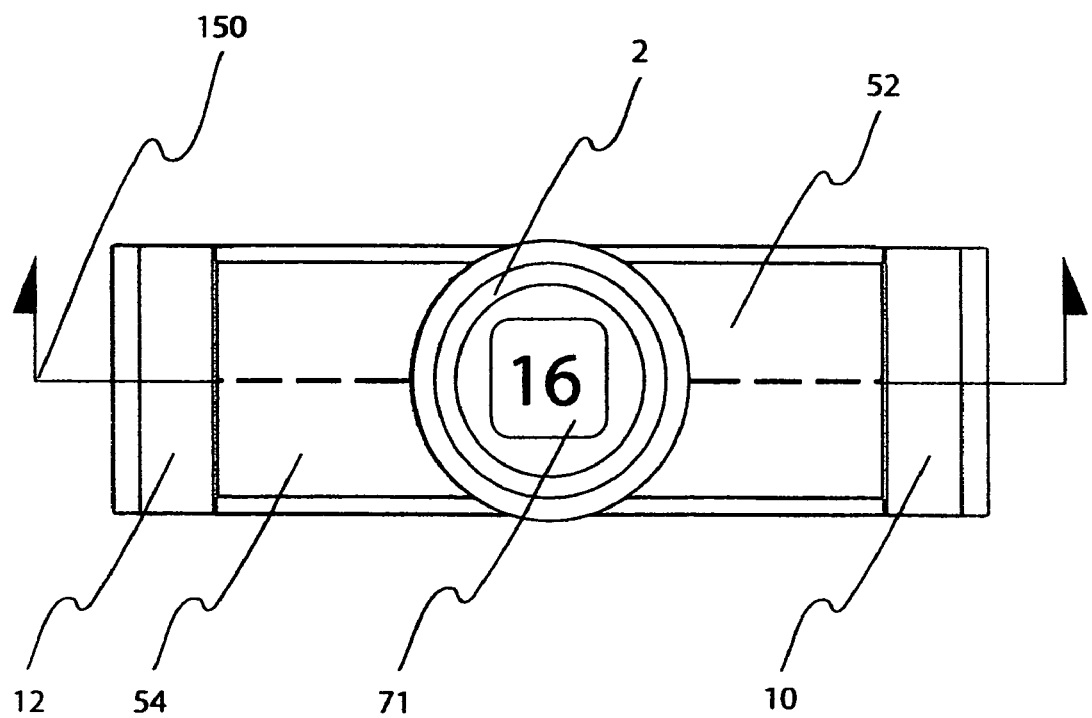
FIG. 9 is a top view of the first embodiment of the eyedropper device of the present invention.

FIG. 2 shows a front section view of the invention 100 as defined by section line 150 shown in FIG. 9. Solution holding bladder 34 is located in the top portion of the housing 52. A pump assembly comprising an inwardly direct check valve 38, and an outwardly directed check valve 37 and resilient tube 40 is located in the central portion of the housing 52. A slidable piston 7 is spring biased 32 and terminates at its top portion in a push button 2 that includes a standard counting device 71. Each time the push button 2 is pushed down, tip 73 engages floor 75 which advances the counter one by one number. In this way, the user can keep track of how many dispensing events he has engaged in and therefore estimate how many dispensing events are left within the unit 100. The opposite end of piston 7 terminates in a pump actuator tip 60 that engages at a right angle horizontally disposed resilient pump tube 40. Bottom tube retainer 78 holds tube 40 in place when the top of tube 40 is pushed down by piston tip 60. A solution transfer tube 74 carries solution from bladder 34 to left intake check valve 38. Upper exit tube 76 carries solution from outgoing check valve 37 to lower exit tube 80 which is surrounded by rigid tube 16. Lower exit tube 80 terminates in rubber stopper 25. Cap 72 can be removed for filling bladder 34 with solution and then be replaced when bladder 34 is full.

Figure 3:
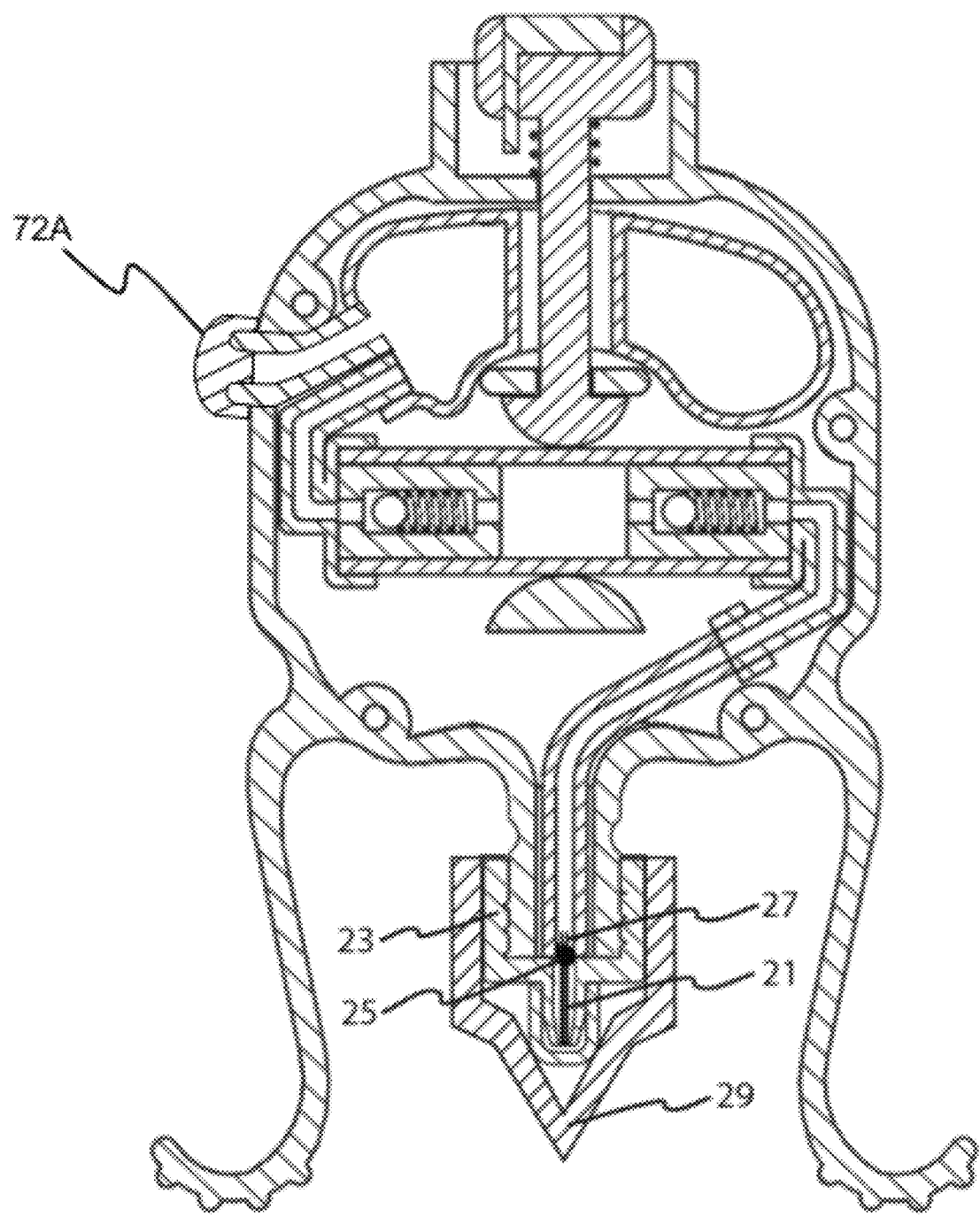
FIG. 3 is a front section view of the first embodiment of the eye drop device with sterile tip and tip cover in place.

FIG. 3 shows the same front section view as in FIG. 2 with a sterile cap assembly comprised of outer cap 29 and threaded cap 23 that includes final needle tube 21. The exit aperture needle tube may preferably consist of eighteen gauge or smaller tubing to decrease the chance of residual drops remaining on the aperture after each use. When the threaded cap 23 is installed by the user, the top portion 27 of needle tube 21 pierces rubber stopper 25 located at the base of lower exit tube 80. The top portion of outer cap 29 is sealed with a peal off label, not shown, keeping the threaded cap 23 and attached needle tube 21 in a sterile condition until the time of use. The entire sterile cap assembly is removed after use and a new sterile cap assembly is installed at the time of the next use. This type of replaceable sterile cap system is known and accepted as proper sterile procedure. This system can currently be found in the product "Forteo" teriparatide injection, manufactured by Lily France SAS.

This system insures that this version of the eyedropper of the present invention remains sterile for each use. This form of tip that maintains sterility can be applied, if so desired, to any or all embodiments of the invention shown below.

FIG. 3 also shows an alternate embodiment of the location of the bladder fill cap 72A so that a person can fill or re-fill the bladder 34 without having to open the housing half 54.

Figure 4:
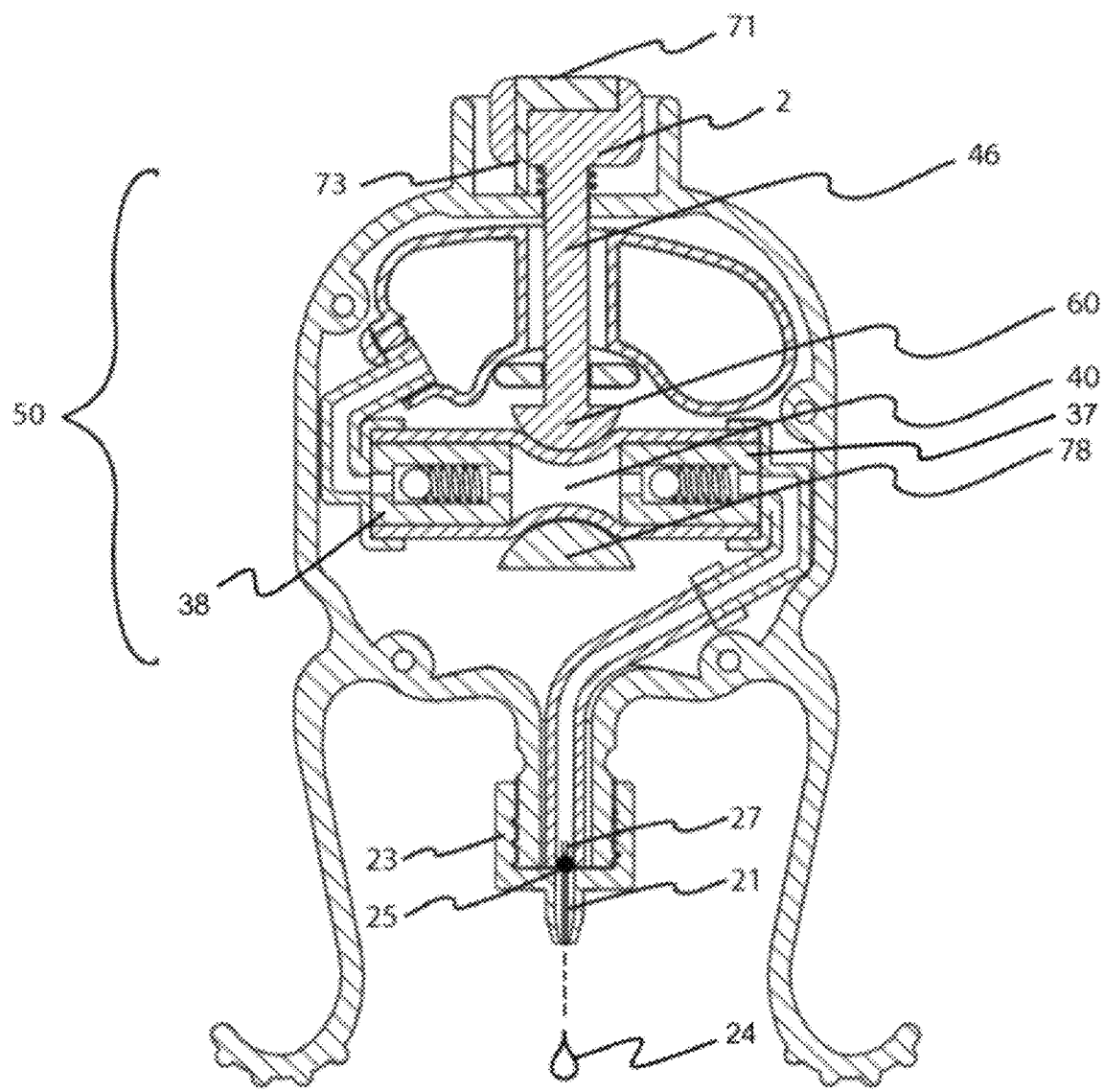
FIG. 4 is a front section view of the first embodiment of the eye drop device with a precise amount of eye drop solution exiting the device.

FIG. 4 shows a section view of the first embodiment after a person has pressed down on push button 2 causing deformation of resilient pump tube 40 forcing a precise amount of solution out of check valve 37 and out of exit tip 21 as shown by droplet 24. When the push button 2 is released by the user, the resulting suction caused by tube 40 returning to its original position forces a new amount of solution into incoming check valve 38. Because solution bladder 34 is made of resilient material such as latex rubber, the bladder 34 can collapse as the solution contained within the bladder diminishes. In this way, no air needs to enter the system thereby insuring that the dispensing of solution remains precise and air free.

Figure 5:
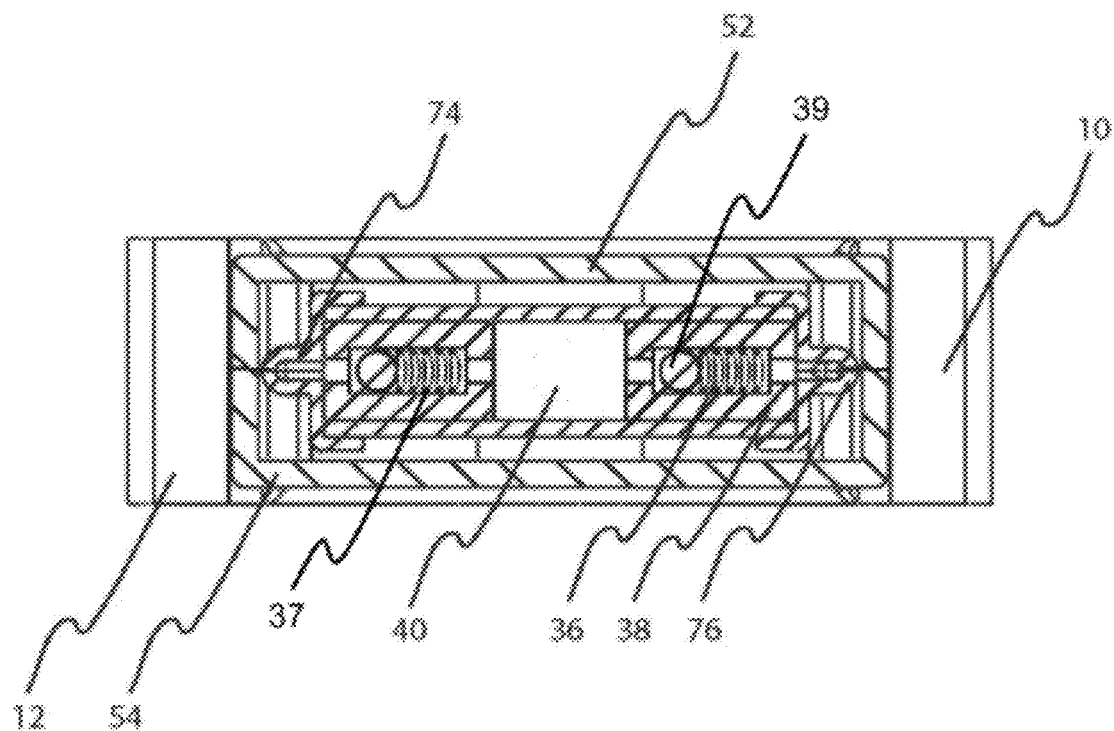
FIG. 5 is a top section view of the first embodiment of the eye drop device with the pump assembly in the ready position.
Figure 8:
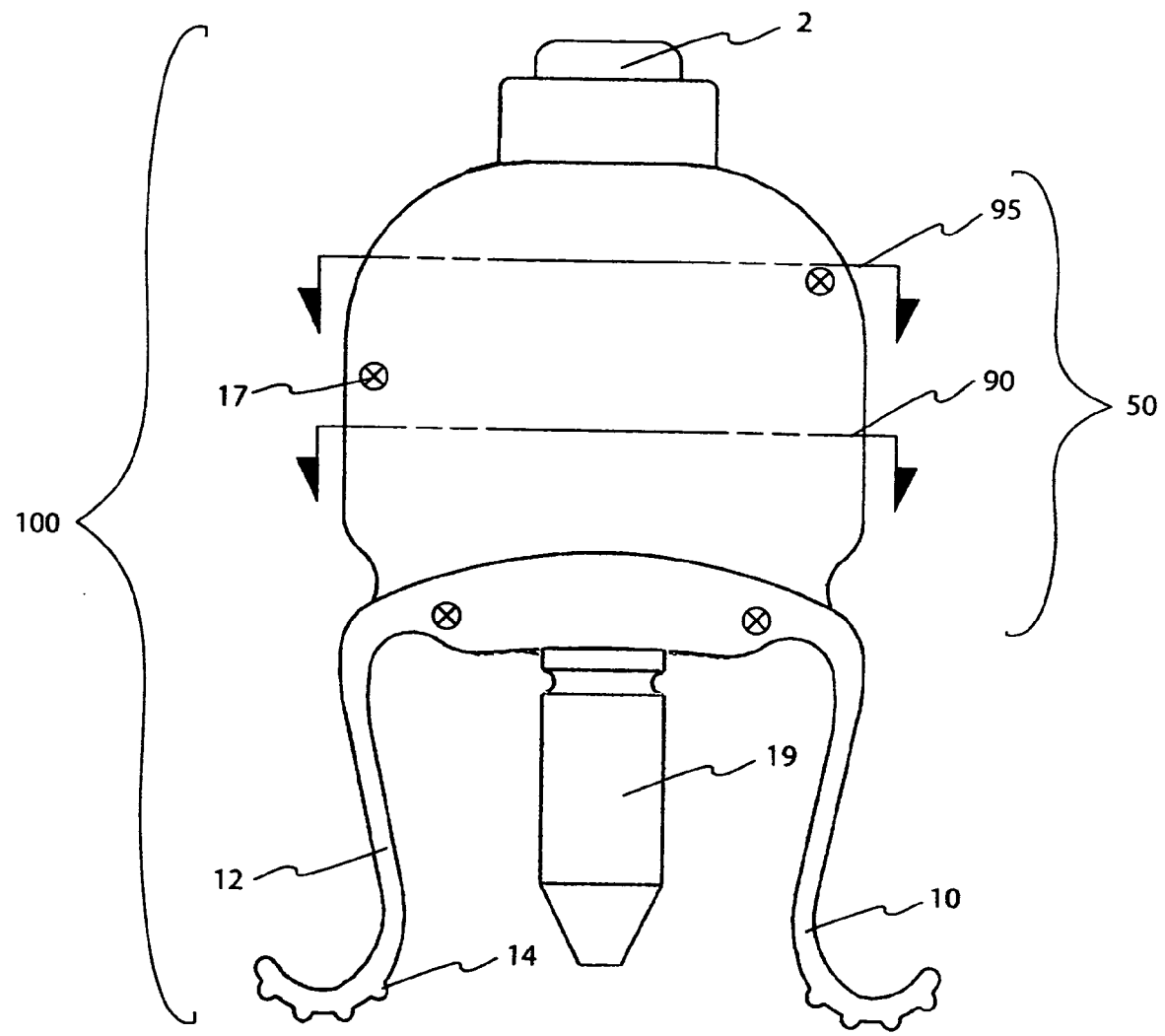
FIG. 8 is a front view of the first embodiment of the eyedropper device of the present invention.

FIG. 5 shows a top section view as defined by section line 90 shown in FIG. 8. Tube 40 is clearly shown to be enclosed within housing halves 52, 54. Identical Check valve bodies 37, 38 include standard compression spring 36 and valve ball 39. Valve entrance tube 74 can be seen as well as exit tube 76.

Figure 6:
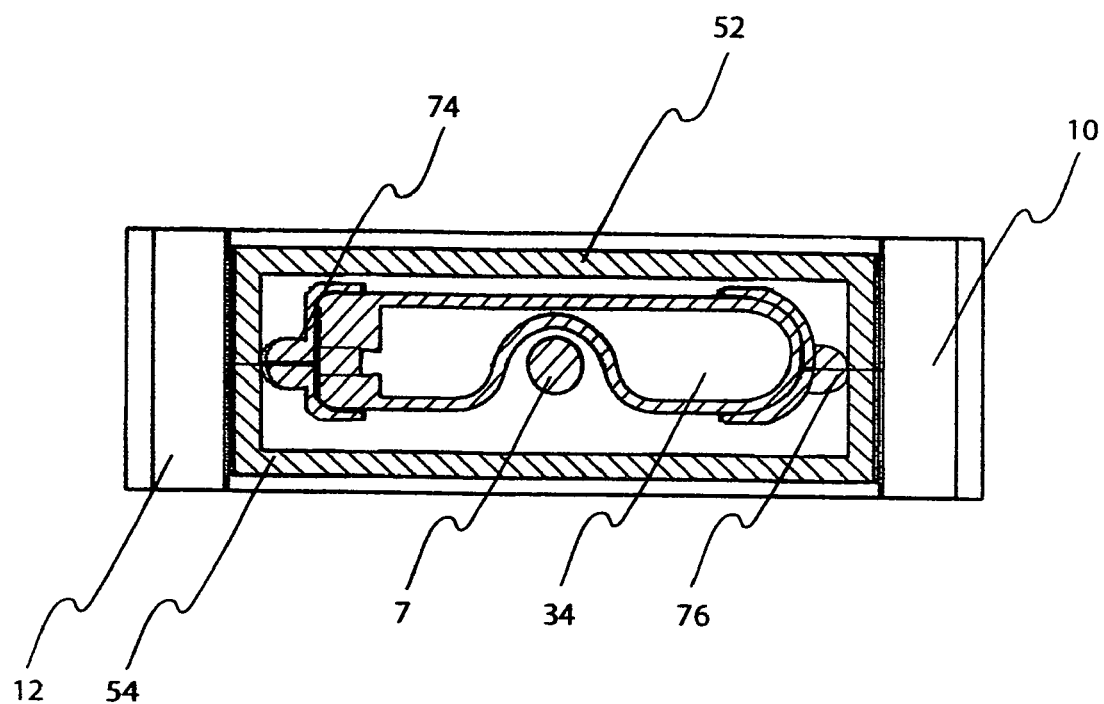
FIG. 6 is a top section view of the first embodiment of the eye drop device showing the resilient solution holding bladder.

FIG. 6 shows another top section view as defined by section line 95 shown in FIG. 8. This view shows how bladder 34 deforms to accommodate piston 7.

Figure 7:
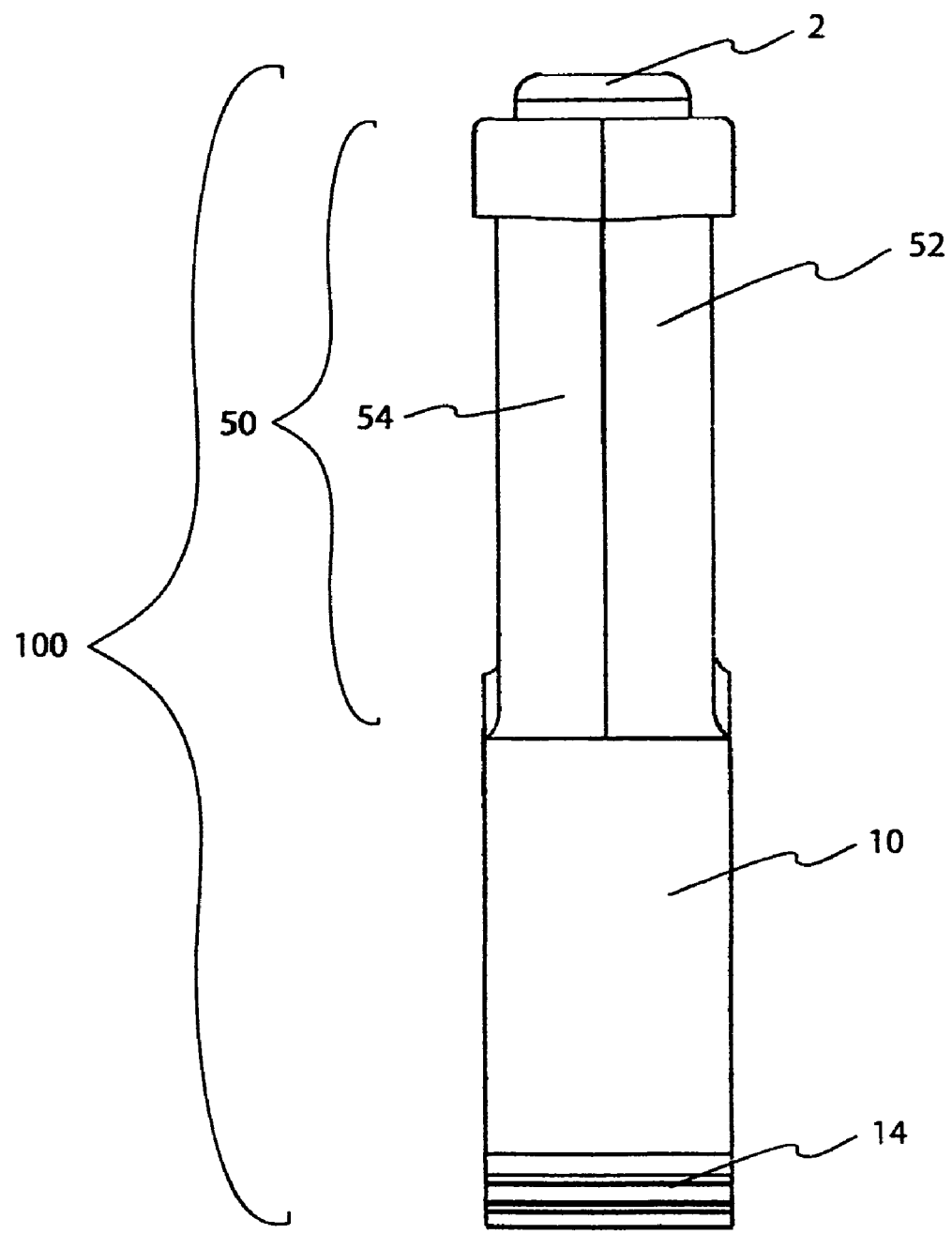
FIG. 7 is a side view of the first embodiment of the eyedropper device of the present invention.

FIG. 7 shows a side view of the first embodiment of the invention 100. Housing halves 52, 54 can be clearly seen.

FIG. 8 shows a front view of the first embodiment of the invention 100. with storage cover 19 in place. The housing halves 52, 54 are held together by screws 17 or other standard fasteners. Resilient molded plastic legs 10, 12 can be clearly seen as well as traction tips 14 which are constructed of high friction material such as rubber.

FIG. 9 shows a top view of the first embodiment of the invention where counter numbers 71 can be clearly seen through a window on the top of push button 2.

Figure 10:
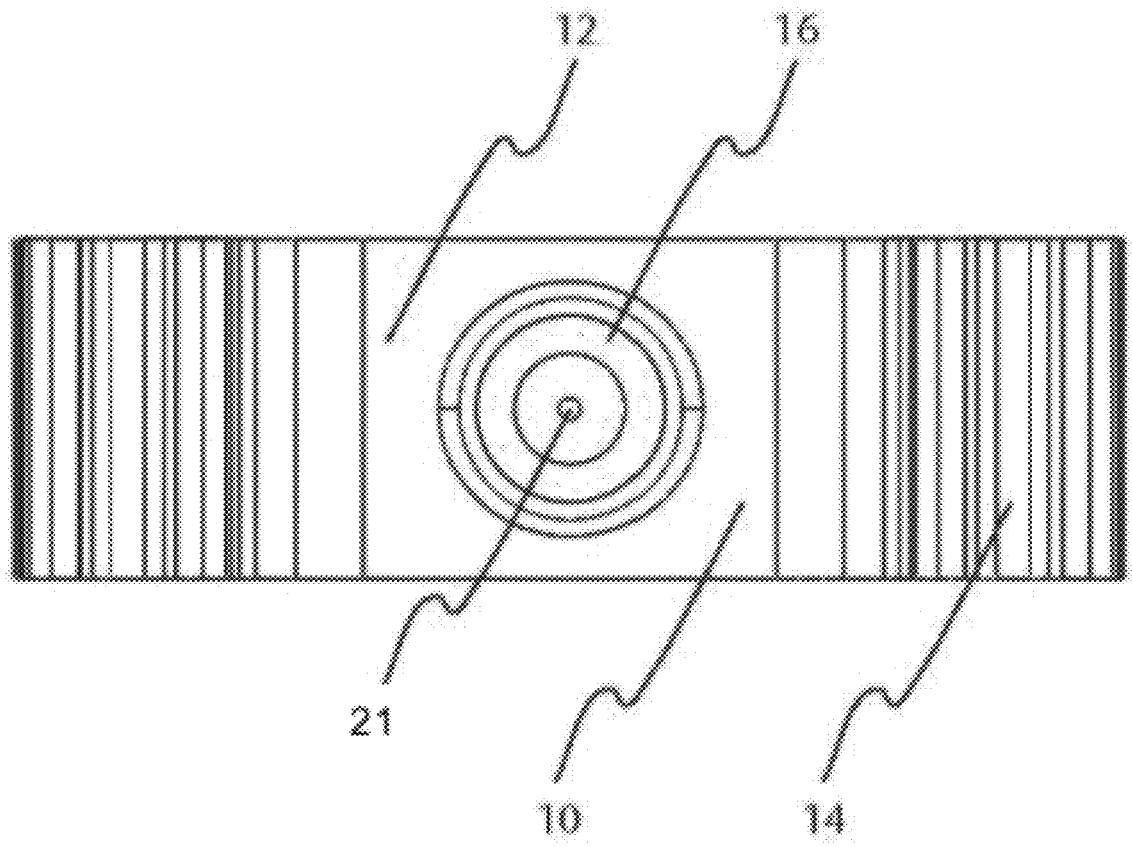
FIG. 10 is a bottom view of the first embodiment of the eyedropper device of the present invention.

FIG. 10 shows a bottom view of the first embodiment of the invention where traction strips 14 can be clearly seen as well as needle tube 21 and rigid tube 16.

Figure 11:
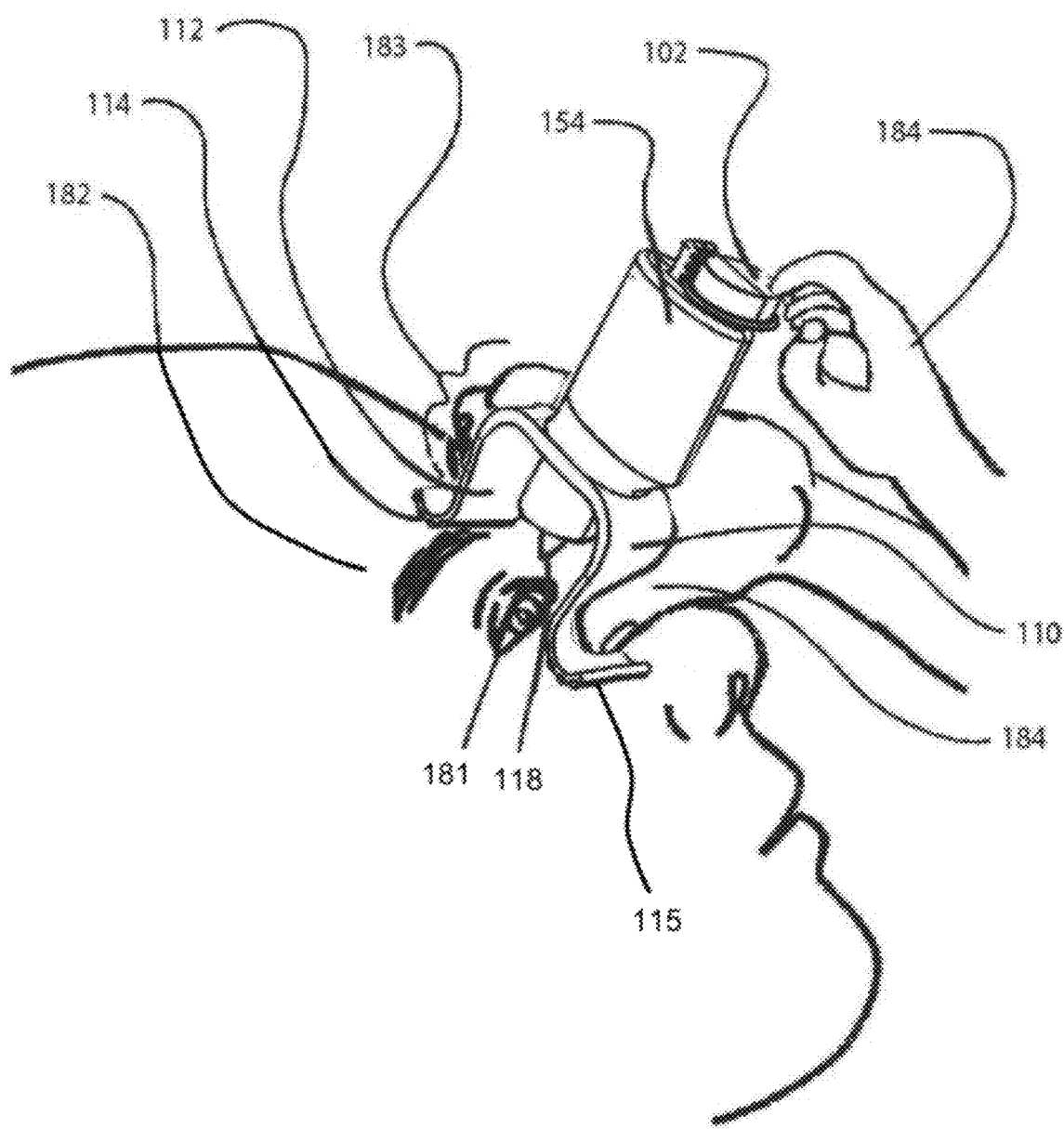
FIG. 11 is a perspective view of a person using an alternate version of the first embodiment of the eyedropper of the present invention.

FIG. 11 shows a perspective view of a person 182 getting ready to administer a precise amount of solution to her eye 181 using a second variation 200 of the first embodiment of the invention. The user holds the legs 110, 112 with one hand 183, 184 as shown, then squeezes the legs, and then places the traction strips 114, 115 of the legs 410, 412 onto the lower and upper portions of the skin of the orbital ridge by placing strips 114 near the eyebrow and strips 115 near the cheek bone. The skin overlying the orbital ridge is tougher and less likely to be damaged than eyelid skin. The user places the forefinger 184 of her other hand on activation button 102. The location of activation button 102 makes it easy for the user to operate the device with the use of only one finger. The user then releases legs 110, 112 causing the legs to spread outward and make traction strips 114, 115 spread the user's eyelids so that she cannot blink. The configuration and placement of the legs 110, 112 during use provides traction on the skin over the orbit region making it possible to hold the lids open with minimal discomfort to the user. The skin of the eyelids is much thinner than the skin over the orbit and would be more easily damaged if the legs were placed directly on the eyelids. The user has been instructed to gaze upward, thereby bringing the sclera of the eye directly under the fluid aperture. The sclera is less sensitive to irritation from medication than the cornea. After this has been achieved, the user presses on activation button 102 causing a precise amount of solution to quickly exit from aperture 118. With eyelids held apart by legs 110 and 112, the user is less likely to blink and therefore can be more certain that the act of administering eye drop solution will be successful. This leg configuration and lid spreading action is found in all embodiments of the invention shown above and below. The location of the solution exit tip 118 is in close proximity to the eye 181 so that the chance of missing the eye during solution application is minimized. The above described holding and dispensing position anchors and stabilizes the dispenser making it easier for the user to deliver the eye drop solution into his or her eye thereby conserving potentially expensive eye drop solution.

Figure 12:
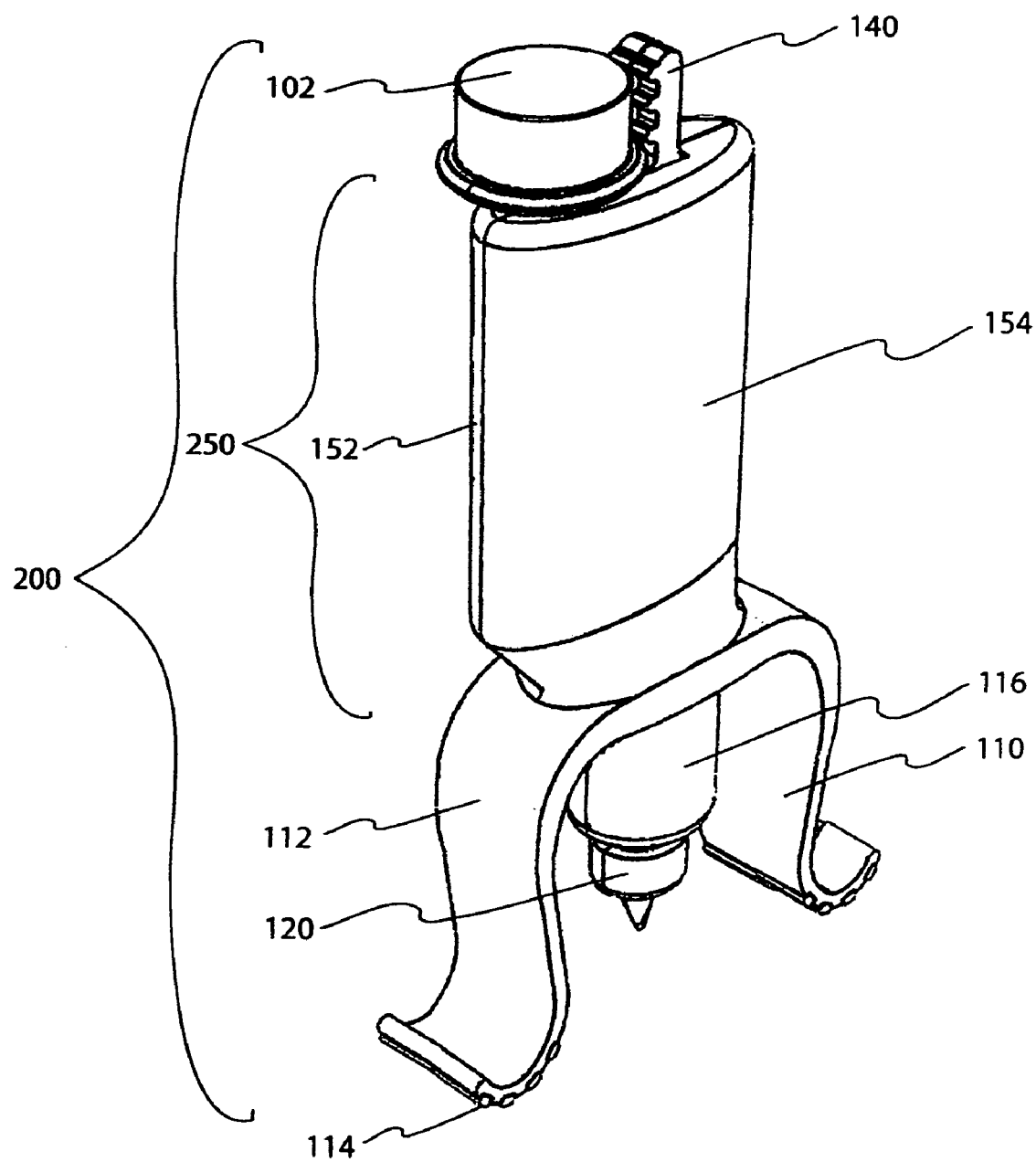
FIG. 12 is a perspective view of an alternate version of the first embodiment of the eyedropper of the present invention.

FIG. 12 shows perspective view of an alternative version of the first embodiment of the invention 200. This version works in a similar way as the original first version however its housing 250 has a more vertical orientation. This version 200 also shows a method of adjusting the amount of solution dispensed by the user as will be explained in detail below.

Figure 13:
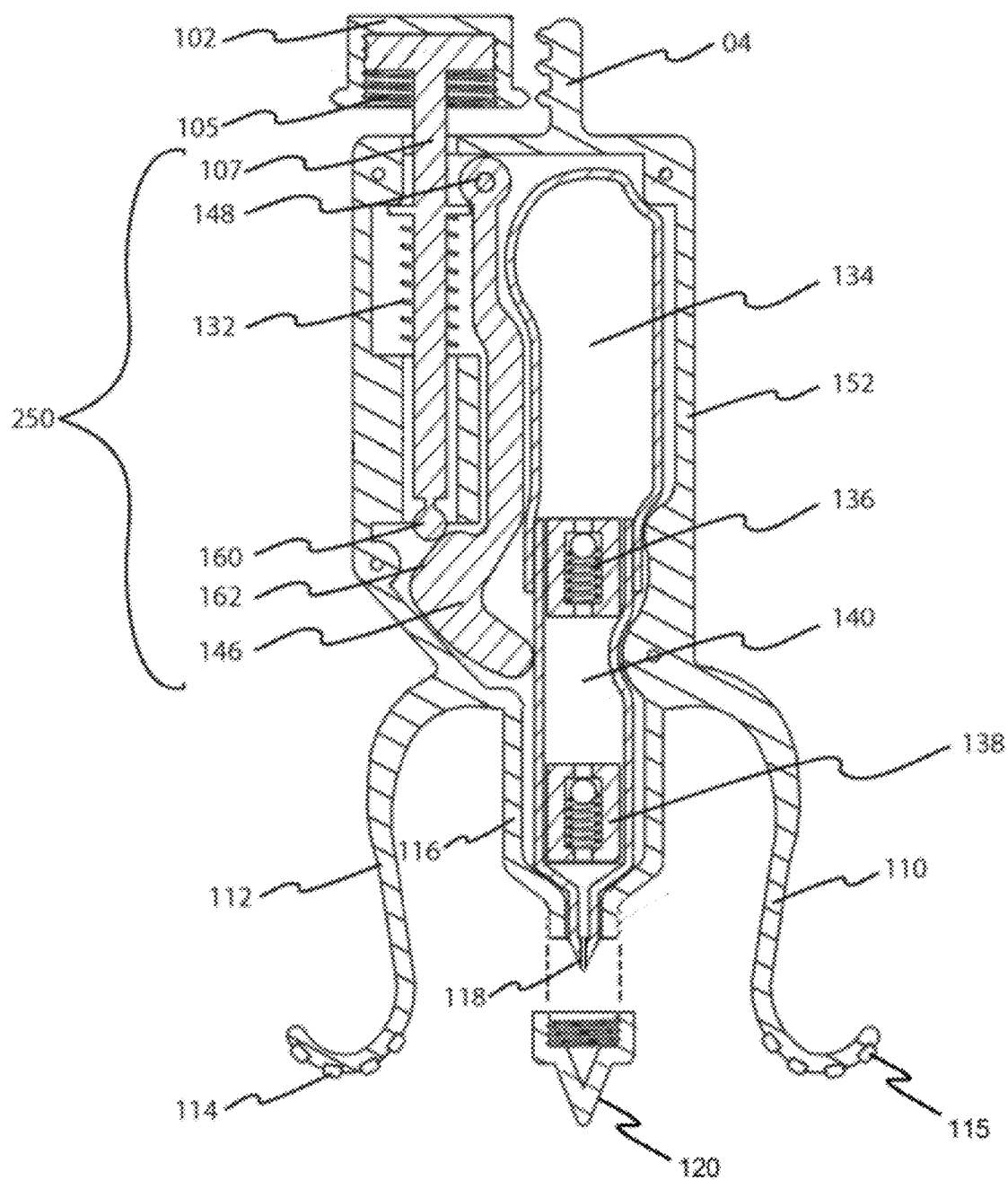
FIG. 13 is a front section view of an alternate version of the first embodiment of the eyedropper of the present invention in the ready position.
Figure 18:
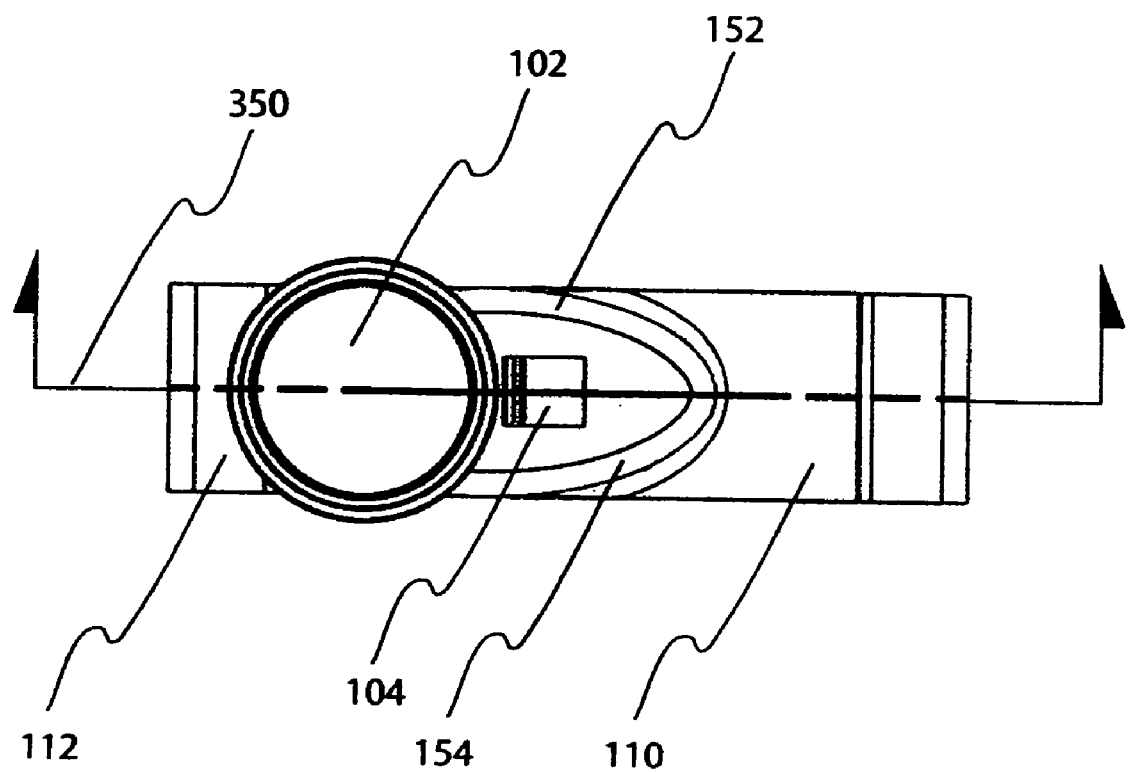
FIG. 18 is a top view of an alternate version of the first embodiment of the eyedropper of the present invention.

FIG. 13 shows a front section view of the alternate version 200 of the first embodiment of the invention as defined by section line 350 of FIG. 18. In this version, the contents of the housing 250 can be seen. The bladder 134 is situated in a vertical format and the pump tube 140 is also situated in a vertical position. This version allows a more direct dispensing of solution with no need for entrance and exit tubes as shown in the first version of the invention 100. In this version 200 the user presses push button 102 (against the return force of spring 132) and piston 107 terminates in a ball member 160 which engages ramp 162 of pinned 148 push foot 146. This embodiment does not show the sterile tip described in the first embodiment, however it can be added if so desired. This version includes a threaded removable and replaceable cap 120 that can engage the mating threads located at the exit portion of tube 116. The check valves 136 & 138, are identical to that of the first version 100. In version 200 push button 102 includes an internal thread 105 that engages mating threads on the piston 107. When the user turns the knob clockwise, he or she reduces the amount of solution delivered when the push button is pressed because the distance the piston travels decreases the movement of the push foot 146 thereby decreasing the amount of incursion into resilient tube 140 and reducing the amount of solution that will be ejected from tip 118. Indicator notches on post 104 help the user determine the amount of solution to be dispensed.

Figure 14:
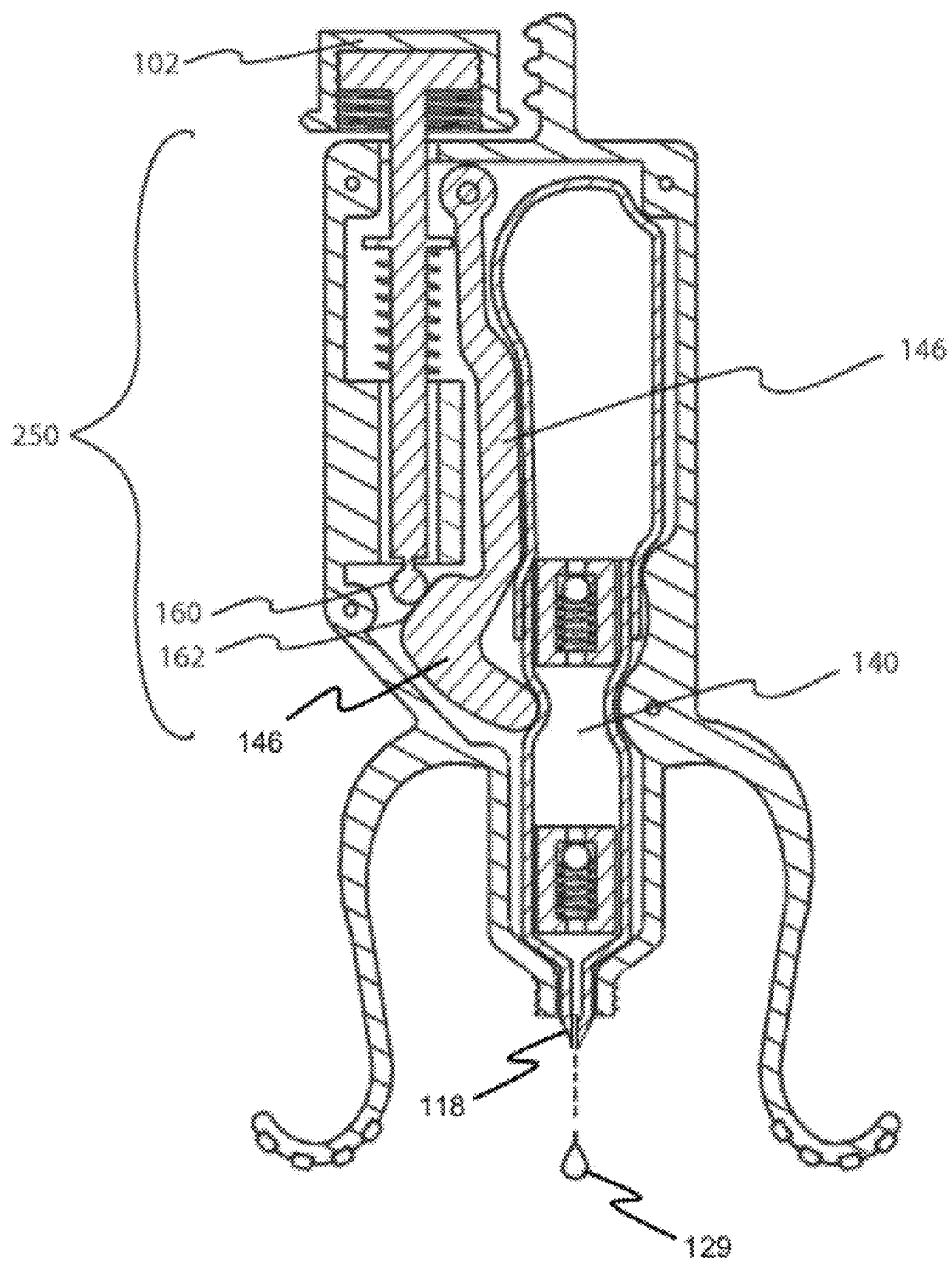
FIG. 14 is a front section view of an alternate version of the first embodiment of the eyedropper of the present invention in the use position.

FIG. 14 shows a the alternate version of first embodiment 200 in the use position where tube 140 has been squeezed by push foot 146 causing a drop 129 of solution to exit from tip 118.

Figure 15:
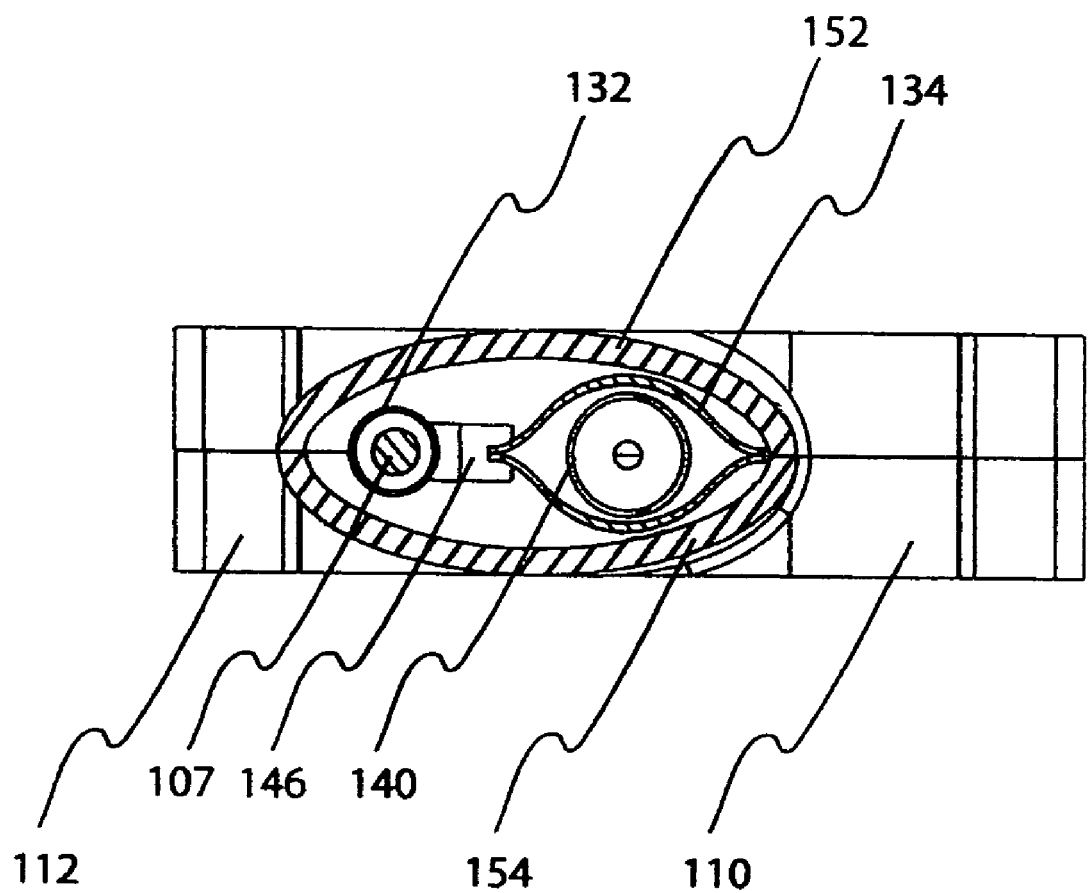
FIG. 15 is a top section view of and alternate version of the first embodiment of the eyedropper of the present invention.
Figure 17:
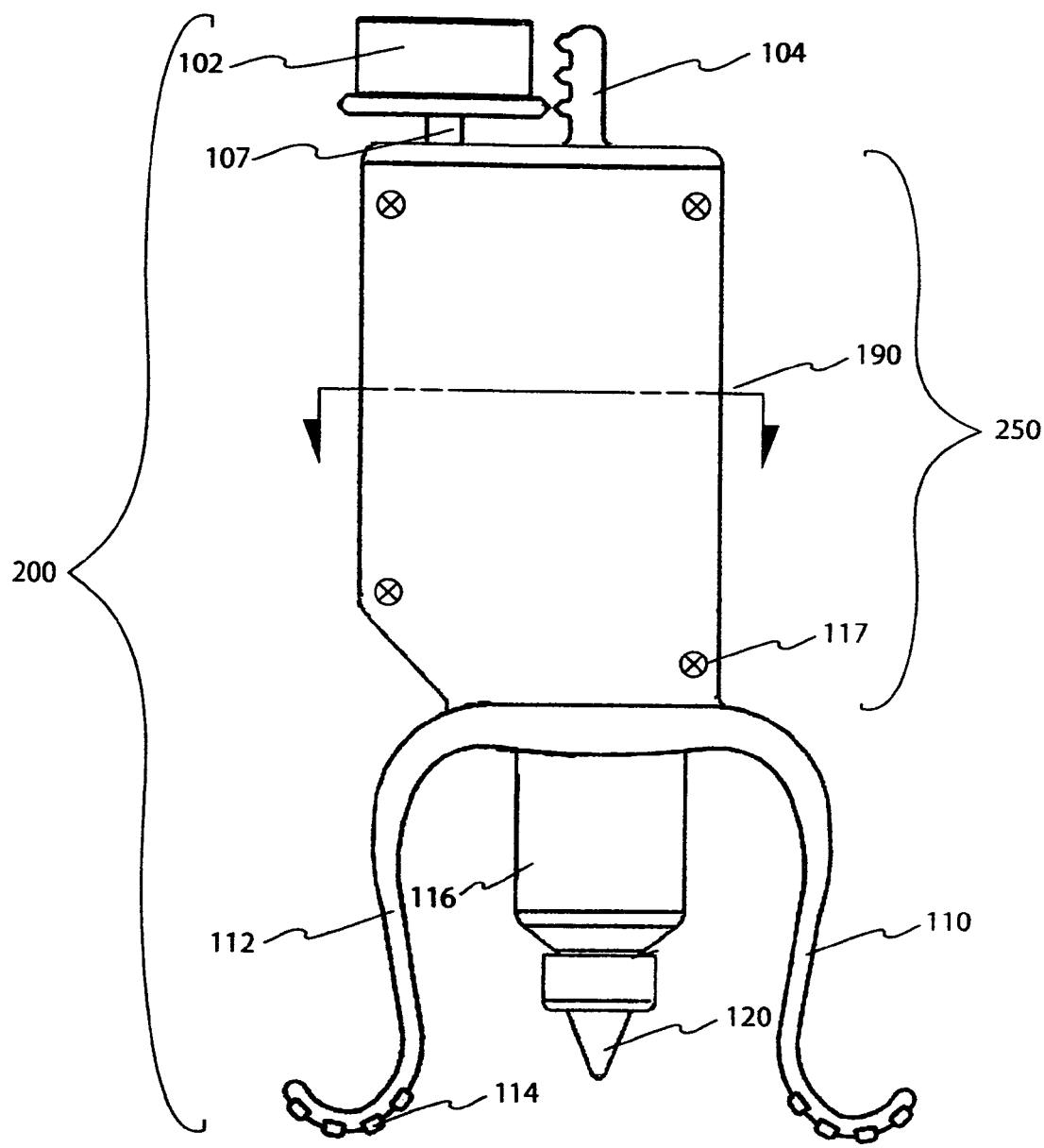
FIG. 17 is a front view of an alternate version of the first embodiment of the eyedropper of the present invention.

FIG. 15 shows a top section view as defined by section line 190 in FIG. 17, housing half's 152, 154 can be clearly seen as well as collapsible bladder 134 and pump tube 140. Push foot 146 can be seen as well as piston 107.

Figure 16:
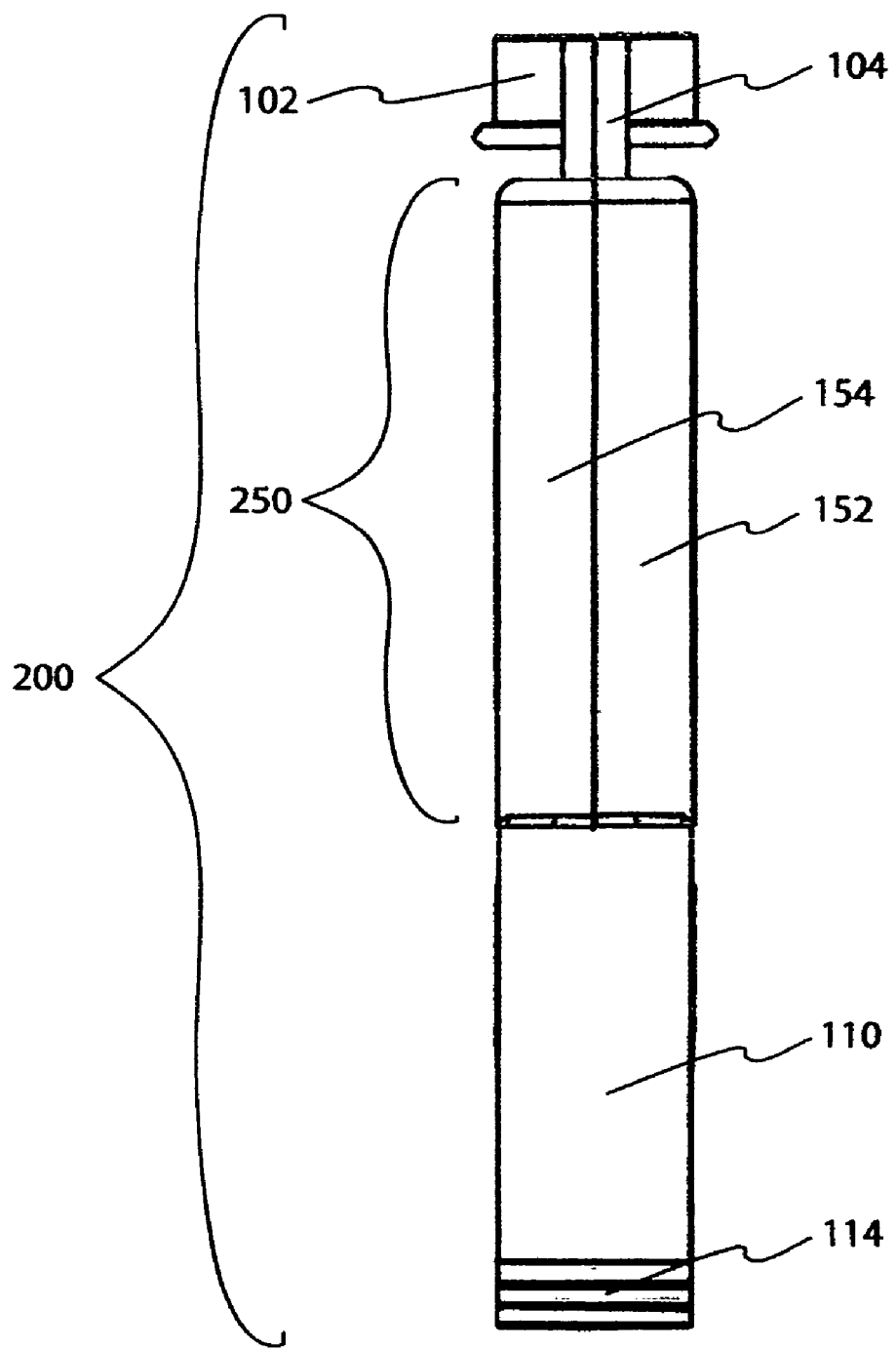
FIG. 16 is a side view of an alternate version of the first embodiment of the eyedropper of the present invention.

FIG. 16 is a side view of the alternate view 200 of the first embodiment of the invention. Housing halves 152, 154 can be clearly seen as well as indicator post 104 and push button 102. Resilient legs 110 are similar to the legs in all other embodiments of the invention as well as traction strips 114.

FIG. 17 is a front view of the alternate version 200 of the first embodiment of the invention. Screws 117 hold housing halves together. Threaded cap 120 can be clearly seen below exit cylinder 116.

FIG. 18 shows a top view of the alternate version 200 of the first embodiment of the invention. Push button 102 can be clearly seen as well as indicator post 104.

Figure 19:
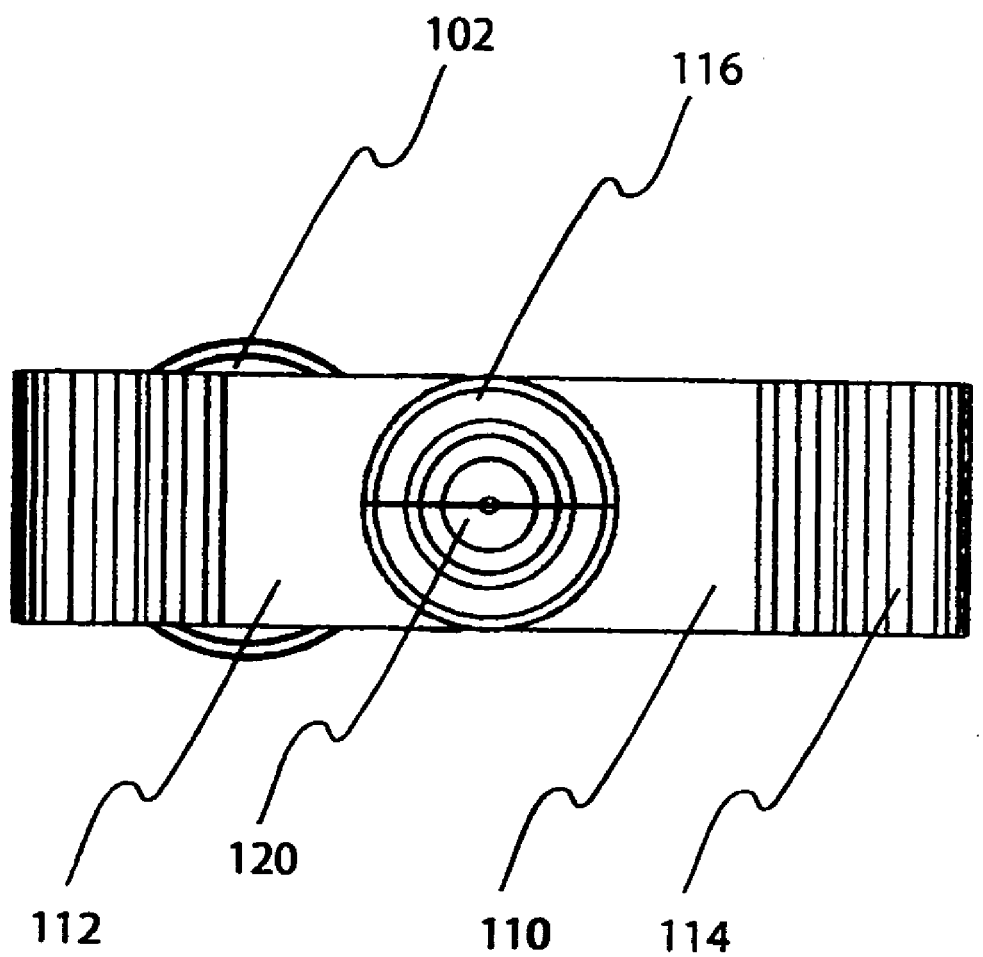
FIG. 19 is a bottom view of an alternate version of the first embodiment of the eyedropper of the present invention.

FIG. 19 is a bottom view of the alternate version 200 of the first embodiment of the invention. Traction strips 114 are similar to all other embodiments of the invention.

Figure 20:
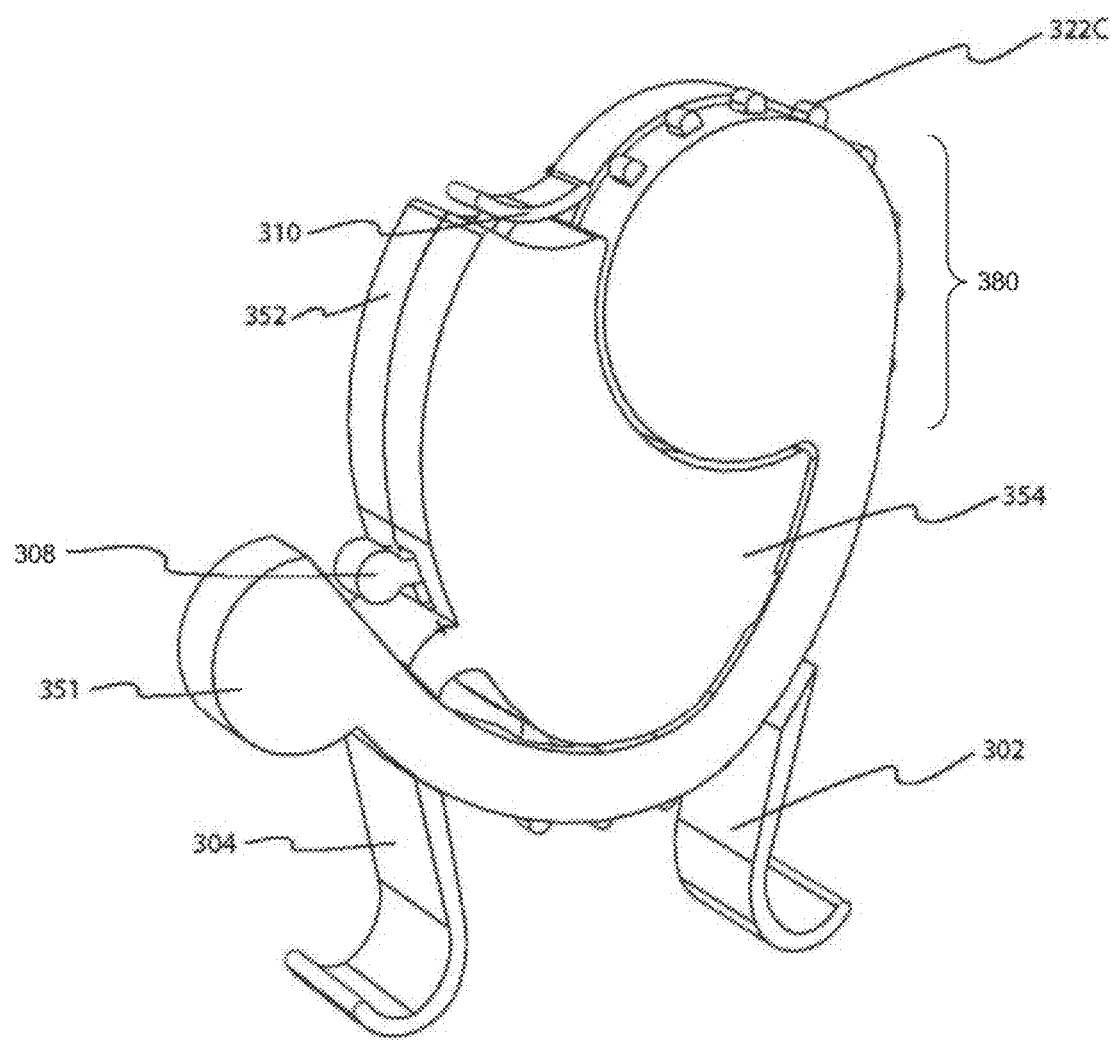
FIG. 20 is a perspective view of a second embodiment of the eyedropper of the present invention.

FIG. 20 shows a second embodiment 300 of the precision eyedropper of the present invention. In this version, a cartridge 380 is removable and replaceable from housing 352, 354. Resilient legs 302, 304 work in a similar way as other versions described above and below. To operate, the user presses on push button 310 to expel a precise amount of sterile eye drop solution. The cartridge 380 contains a plurality of discrete solution holding chambers or ampoules 322 as will be described in detail below. By pressing on lever 308, the user advances the next cartridge to the dispensing position and rolls the previously used cartridge into storage area 351.

Figure 21:
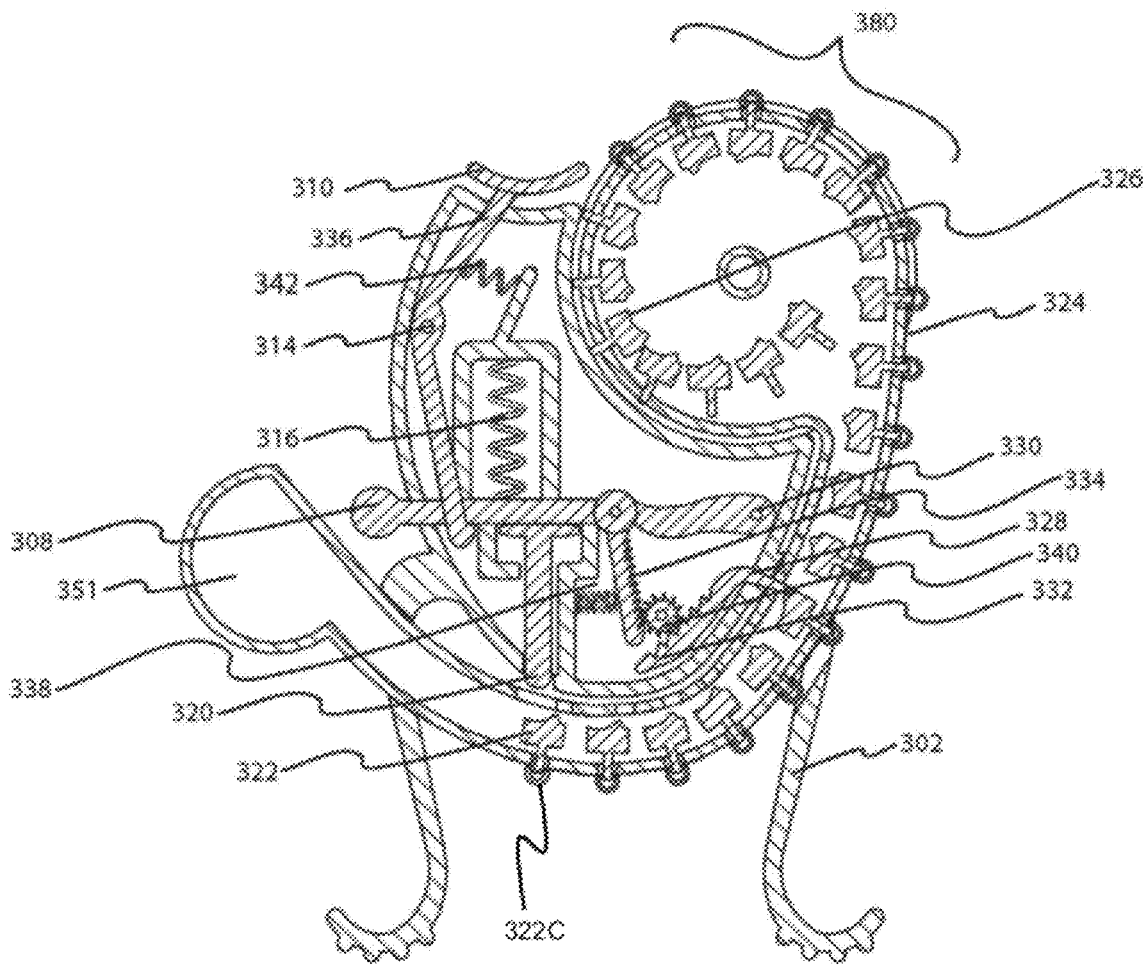
FIG. 21 is a front section view of a second embodiment of the eyedropper of the present invention in the ready position.
Figure 25:
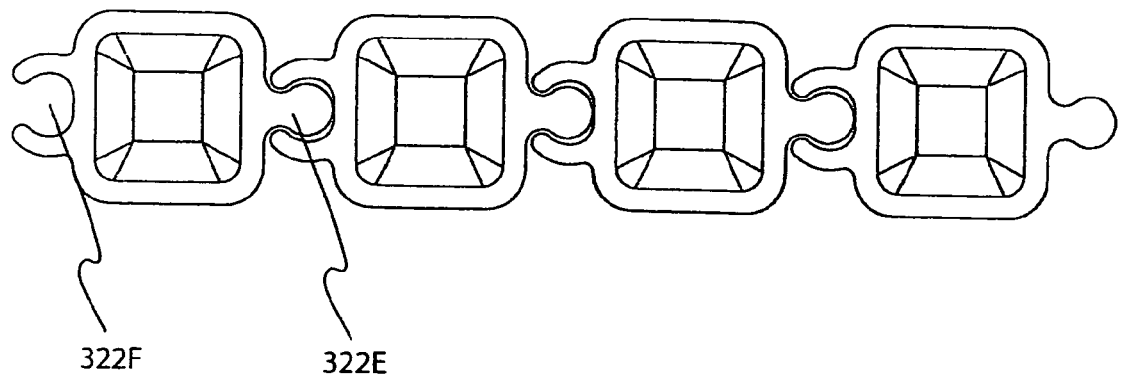
FIG. 25 is a top view of the individual ampoules of the second embodiment of the eyedropper of the present invention.

FIG. 21 shows a front section view of the second embodiment of the invention 300. Ampoules 322 are wound up in a snail like pattern. They are each removably attached to each other as shown in FIG. 25. The ampoules 322 are advanced one at a time until they land under the piston member 338. The advancing mechanism works as follows. When the user lifts up on pinned 330 ever end 308, ratchet arm 334 causes pinion gear 340 to rotate which in turn causes second ratchet arm 332 to be pulled down thereby forcing the curved tip of the second ratchet arm 332 to pull an ampoule 322 down towards the push piston 320. When the lever arm 308 is fully lifted spring 342 biased activation arm 336 becomes locked in the up position when the bottom tip of the arm engages the lever 308 and holds it, and the piston 320, in the ready position. When the user presses on the release push button 310, the pinned lever arm 308 is released and forced downward by spring 316, and forcing piston 320 down onto ampoule 322 and squashing it to cause the solution contained within the chamber to be expelled out and into a person's eye. Before an ampoule 320 is used, the user removes cap 322C. Because each ampoule is capped, the solution remains sterile until just before use.

Figure 22:
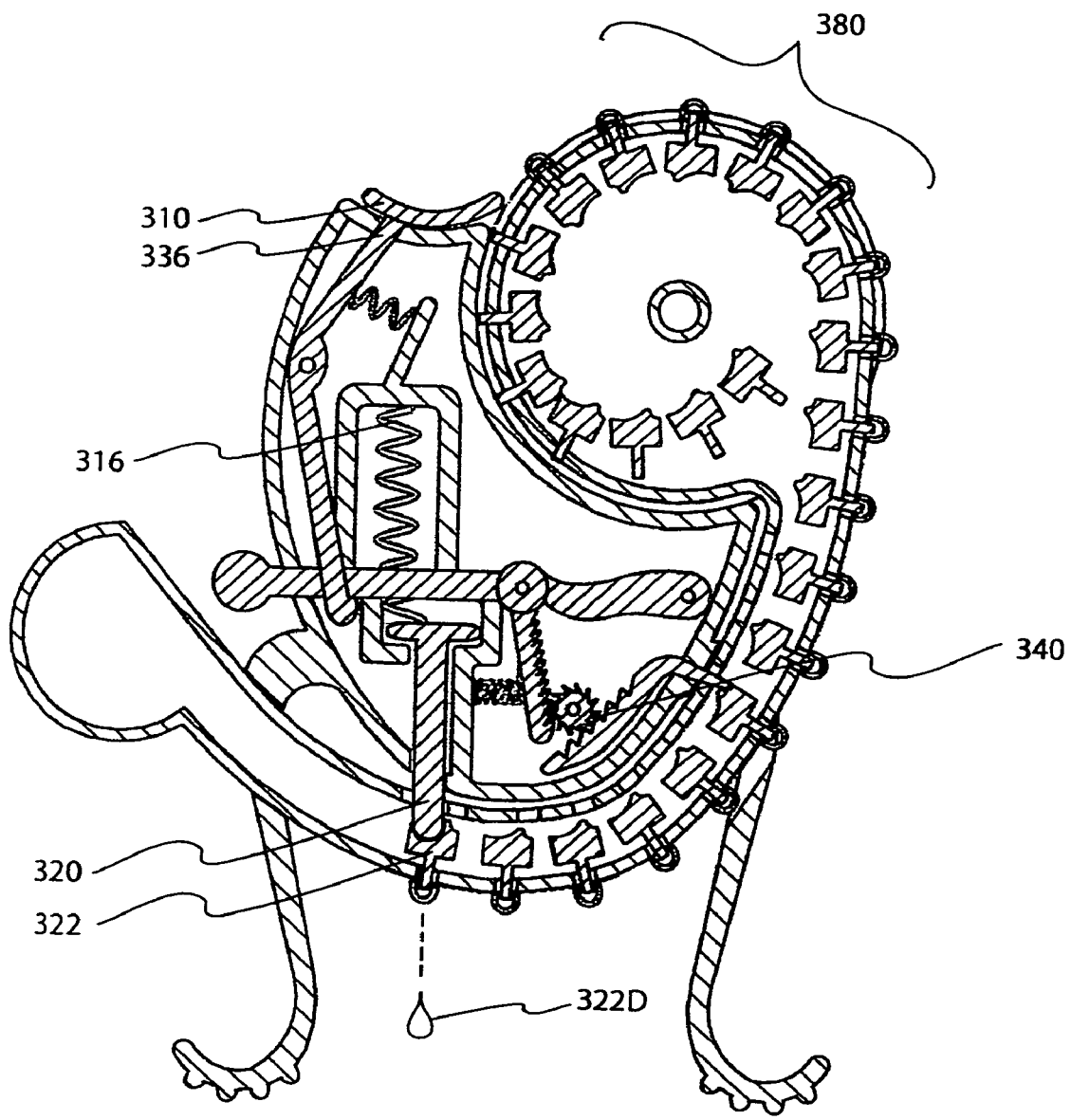
FIG. 22 is a front section view of the second embodiment of the eyedropper of the present invention in the use position.

FIG. 22 shows the second embodiment 300 of the present invention in the use mode. Piston 320 has pressed down on ampoule 322 to expel solution drop 322D.

Figure 23:
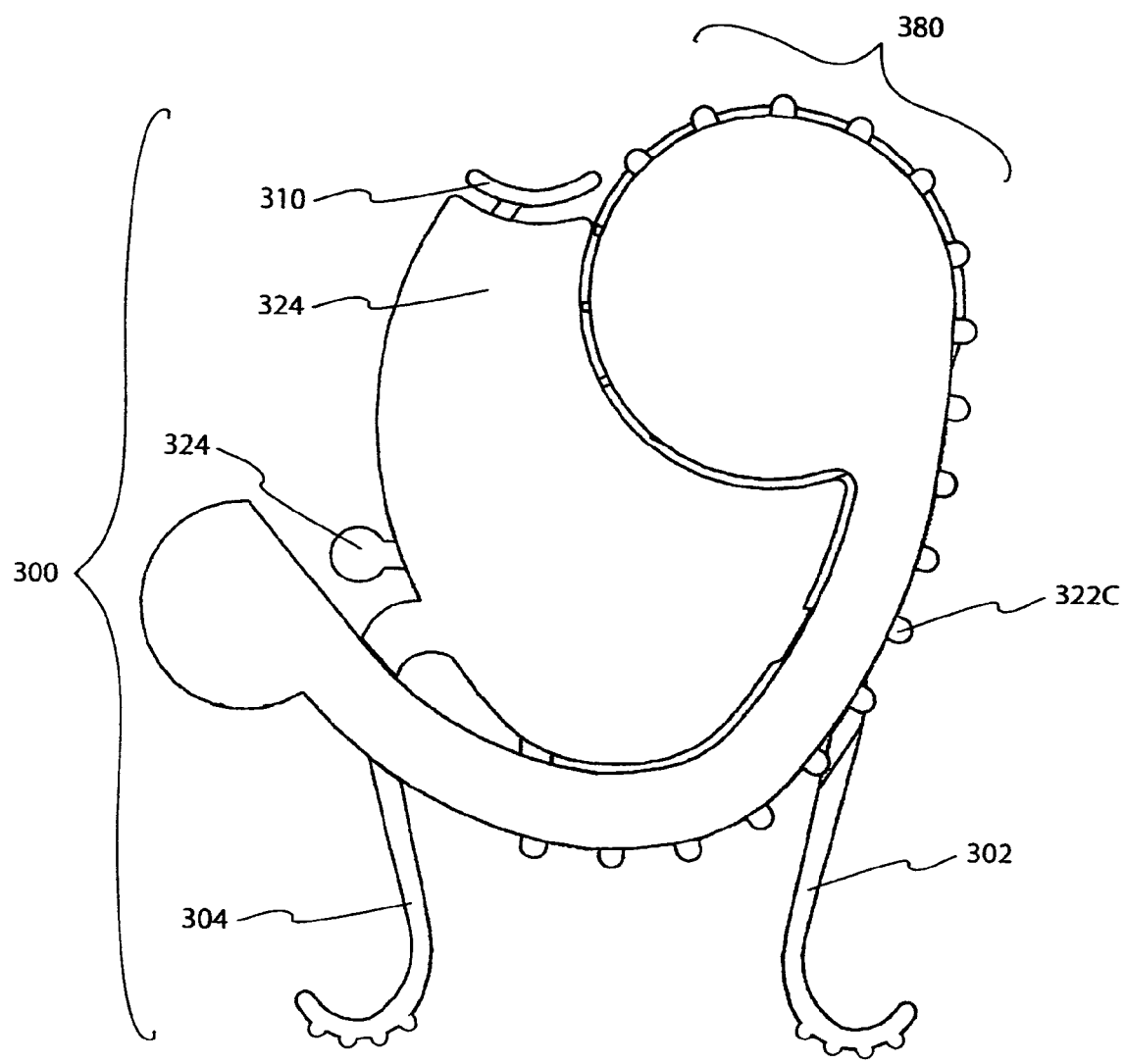
FIG. 23 is a front view of the second embodiment of the eyedropper of the present invention.

FIG. 23 is a front view of the second embodiment of the invention 300. The caps 322C of each chamber can be seen as they make their way to the point where the piston can compress them.

It is important to note that even though this embodiment shows a plurality of ampoules 322 being stored within a cartridge, an embodiment can also be conceived where only one ampoule 322 at a time is inserted into a delivery device by a user, thereby eliminating the need for a main cartridge and an ampoule advancing mechanism.

Figure 24:
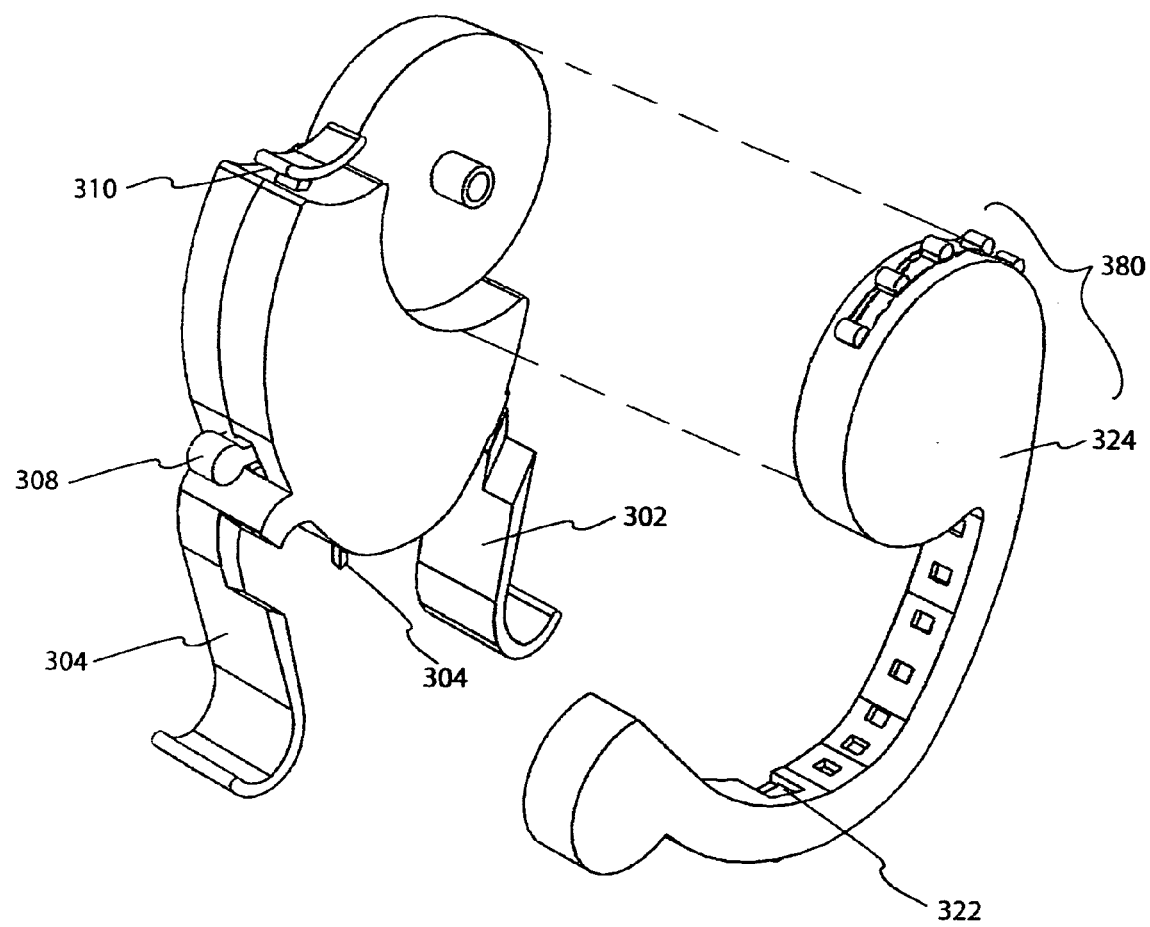
FIG. 24 is an exploded view of the second embodiment showing the cartridge removed from the main housing.

FIG. 24 shows a perspective exploded view of the cartridge version 300. The cartridge 324 can be removed and replaced as necessary.

Figure 26:
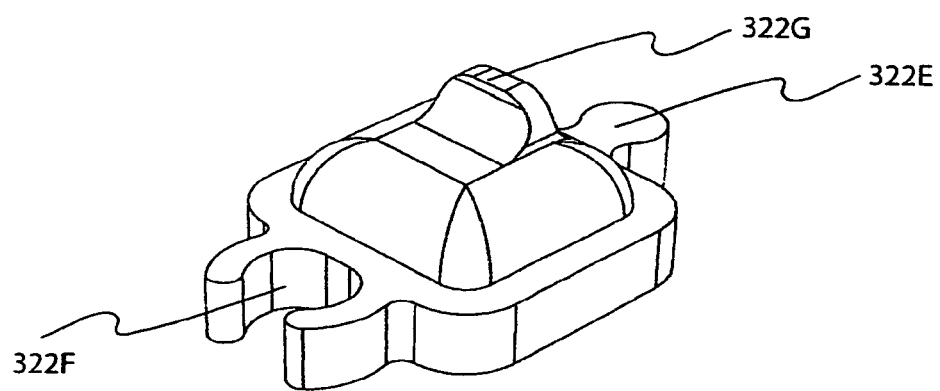
FIG. 26 is a perspective view of a single ampoule of the second embodiment of the eyedropper of the present invention.

FIG. 25 shows a group of ampoules 322 that are connected by nodes 322E and C shaped node retainers 322F. Each ampoule 322 includes an upwardly facing tab 322G as shown in FIG. 26 which engages with the curved ratchet member as described earlier, to advance the ampoule one position for each lever arm movement.

Figure 27:
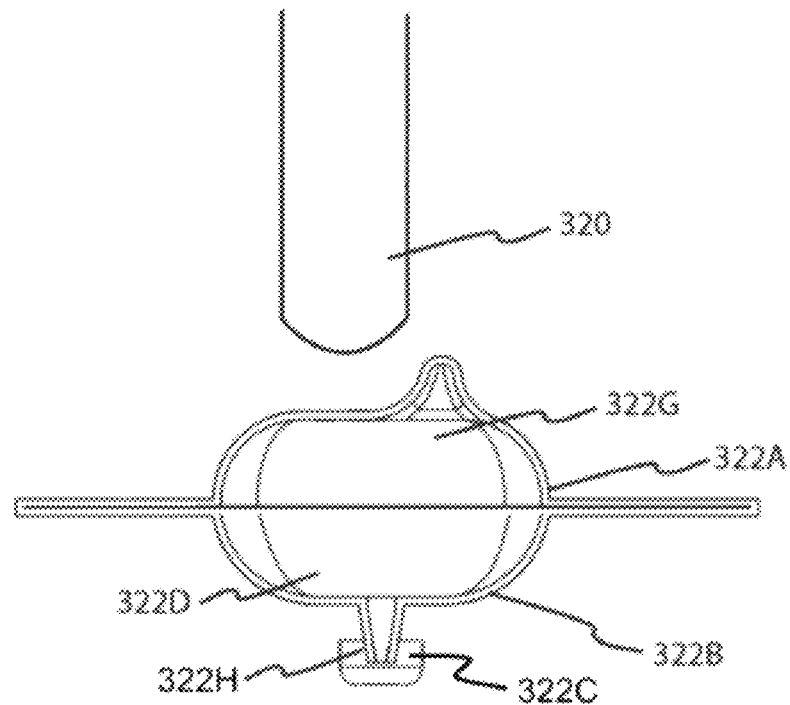
FIG. 27 is a side section view of the ampoule of the second embodiment of the eyedropper of the present invention in the ready position.
Figure 28:
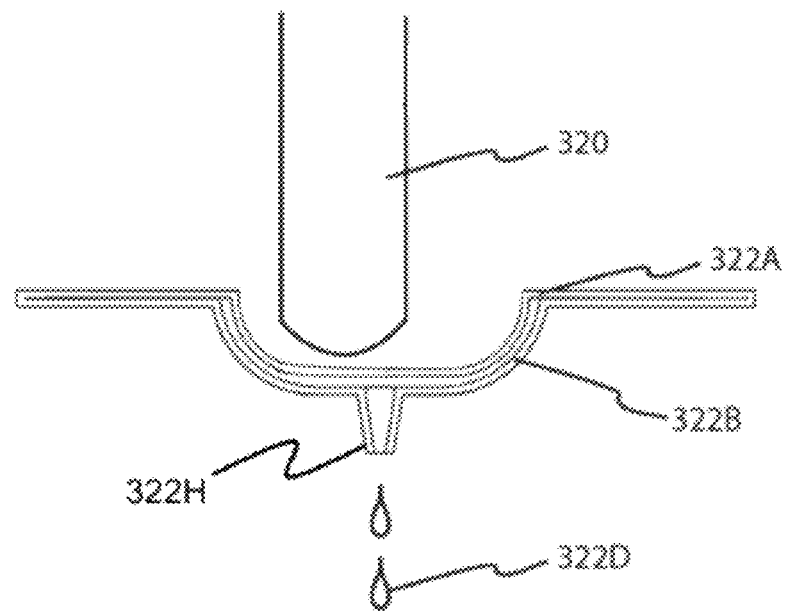
FIG. 28 is a side section view of an ampoule of the second embodiment of the eyedropper of the present invention in the use position.

FIG. 27 shows a side view of an ampoule formed of a top half 322A and a bottom half 322B which is filled with solution. FIG. 28 shows the same ampoule after the piston tip 329 has squashed the ampoule half 322A forcing the solution 322D out of exit aperture 322H.

Figure 29:
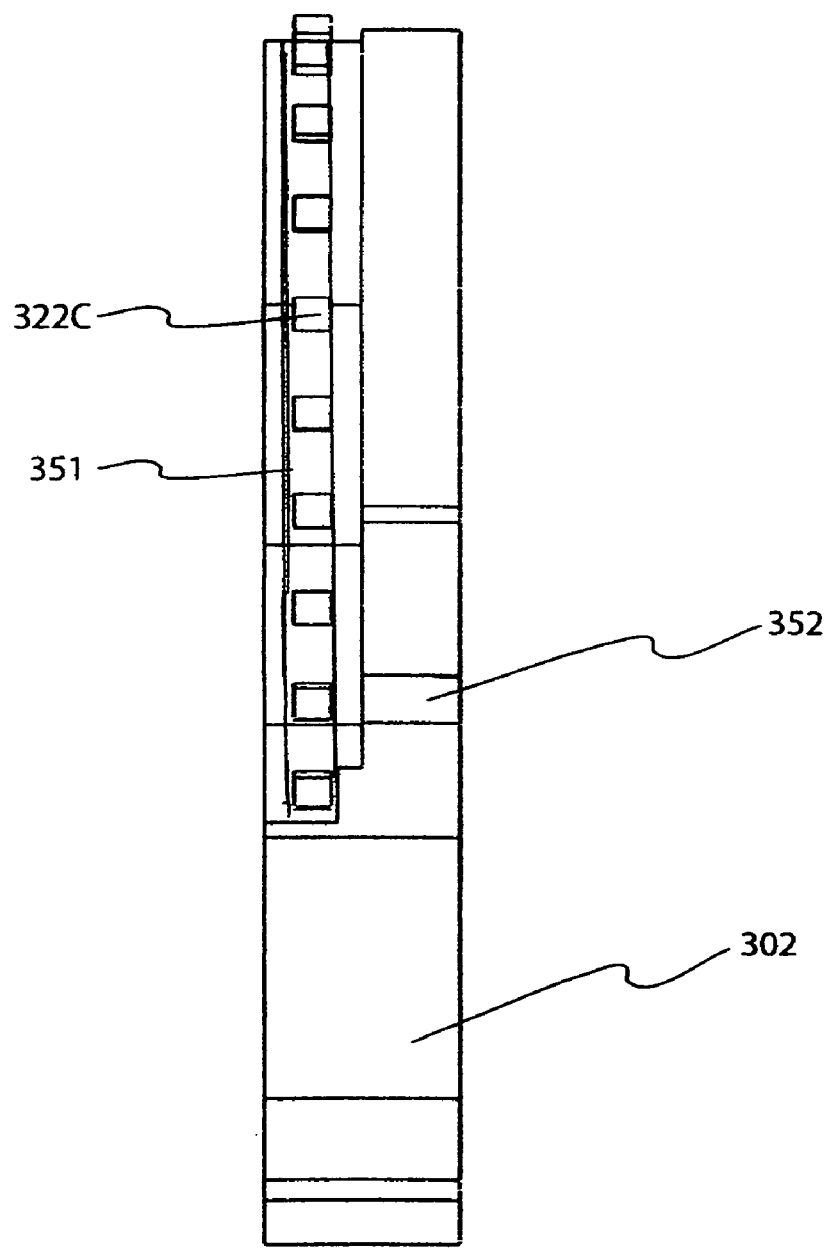
FIG. 29 is a side view of the second embodiment of the eyedropper of the present invention.

FIG. 29 shows a side view of the second embodiment 300 of the invention.

Figure 30:
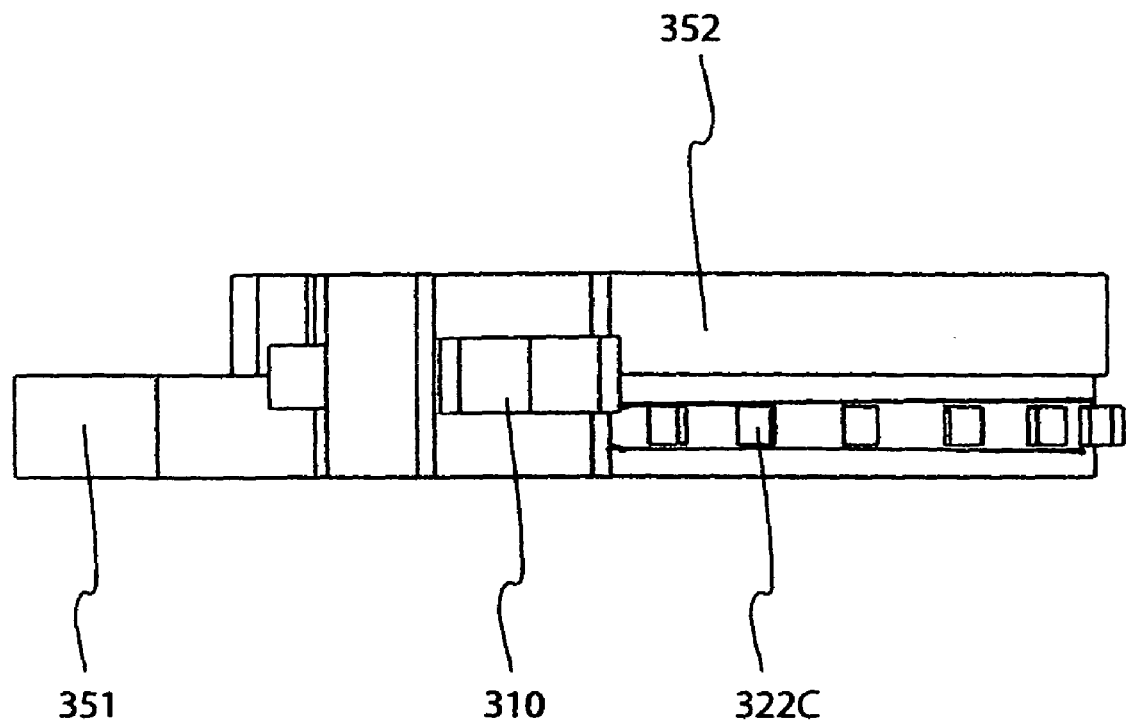
FIG. 30 is a top view of the second embodiment of the eyedropper of the present invention.

FIG. 30 shows a top view of the second embodiment 300 of the invention

Figure 31:
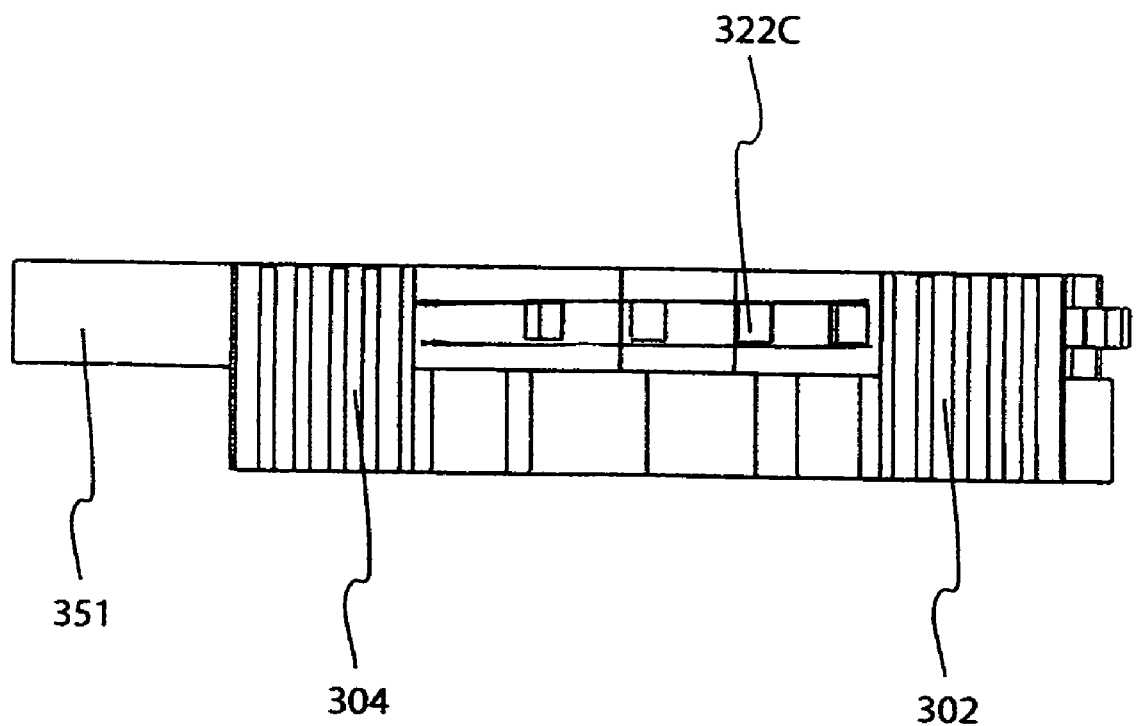
FIG. 31 is a bottom view of the second embodiment of the eyedropper of the present invention.

FIG. 31 is a bottom view of the second embodiment 300 of the invention.

Figure 32:
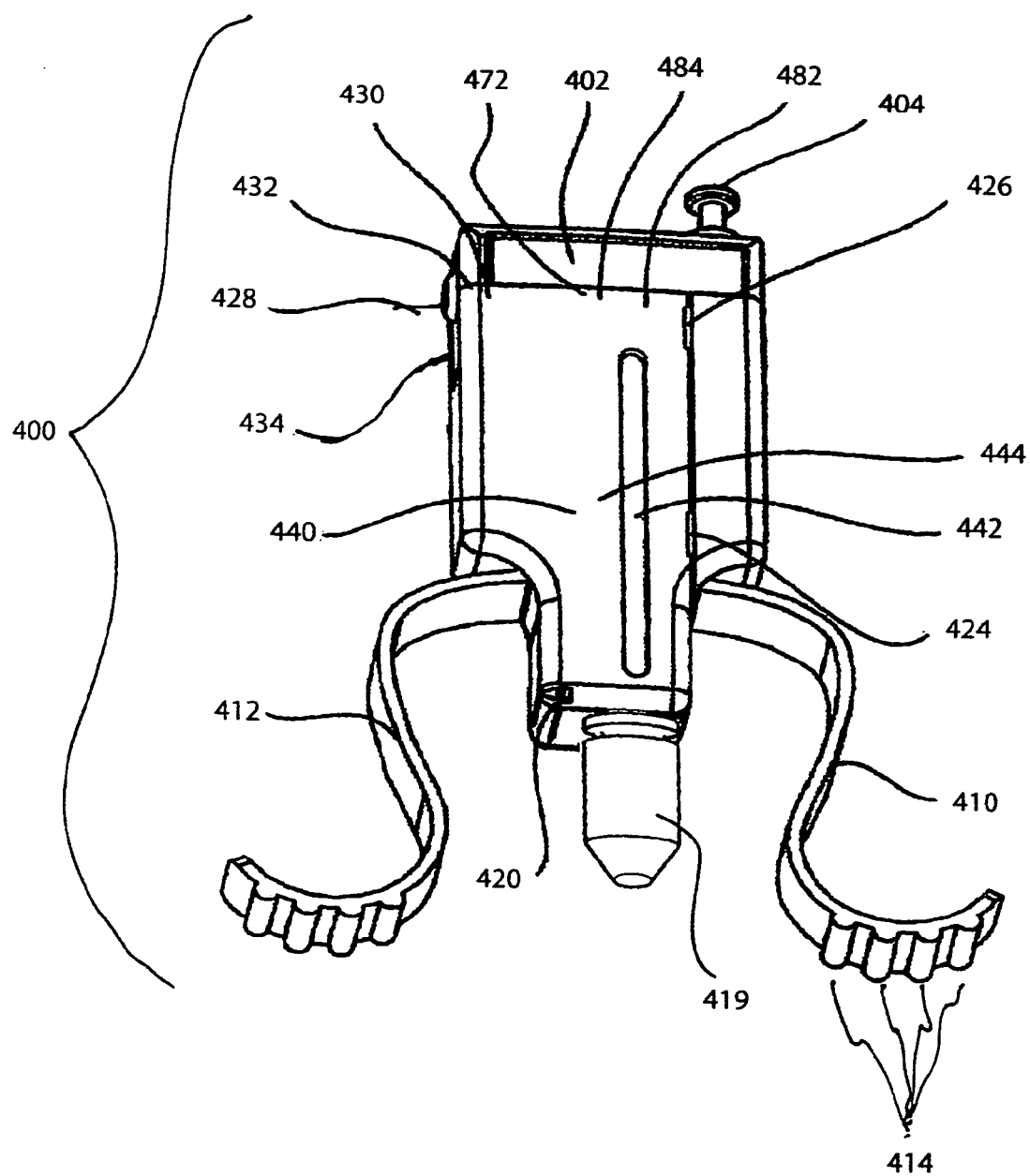
FIG. 32 is a perspective view of a third embodiment of the eyedropper of the present invention.

FIG. 32 is a perspective view of a third embodiment of the invention 400. Front door 440 includes an elongated aperture that allows the user to see the amount of solution 450 left in the cartridge 442 that resides inside the housing. Downwardly facing legs 410, 412 and friction strips 414 operate in a similar fashion to the previous eyedropper embodiments described above. The release of drops by pressing push button 404 will be described in detail below. Tip cover 419 protects the tip from damage and dirt during storage.

Figure 33:
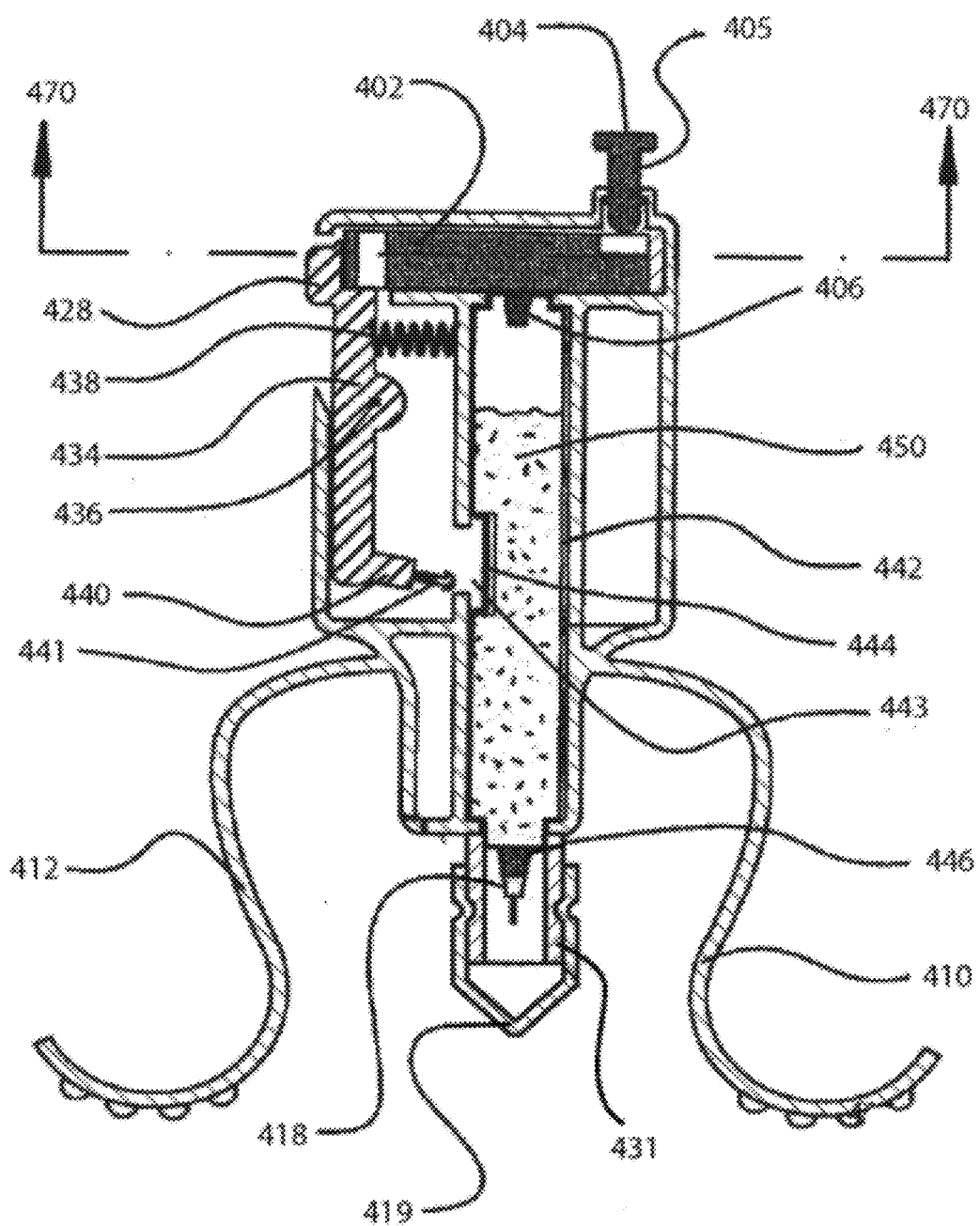
FIG. 33 is a front section view of the third embodiment of the eyedropper of the present invention in the ready position.
Figure 37:
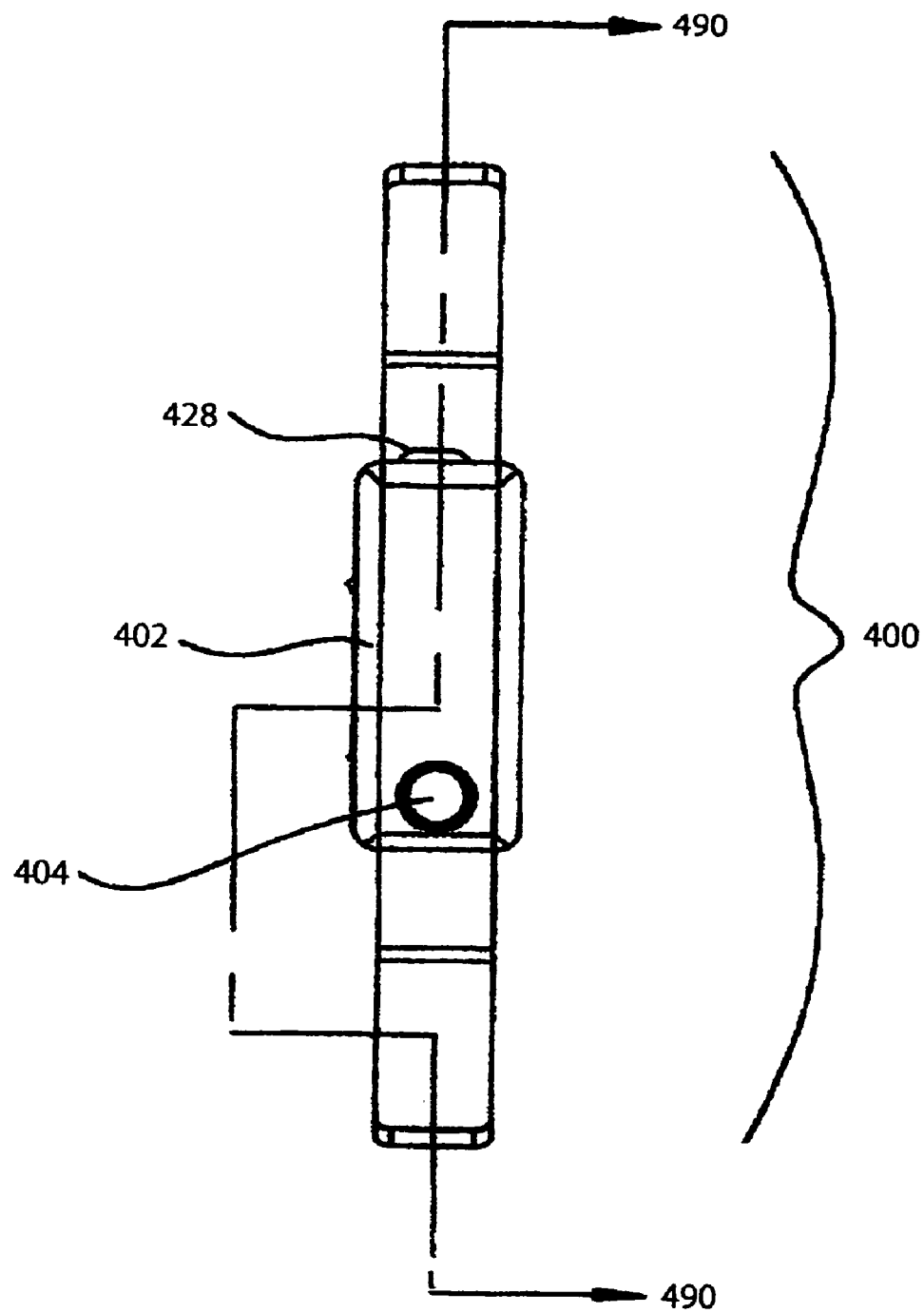
FIG. 37 is a top view of the third embodiment of the eyedropper of the present invention.

FIG. 33 is a front section view of the third embodiment 400 of the invention as defined by section line 490 in FIG. 37.

Figure 34:
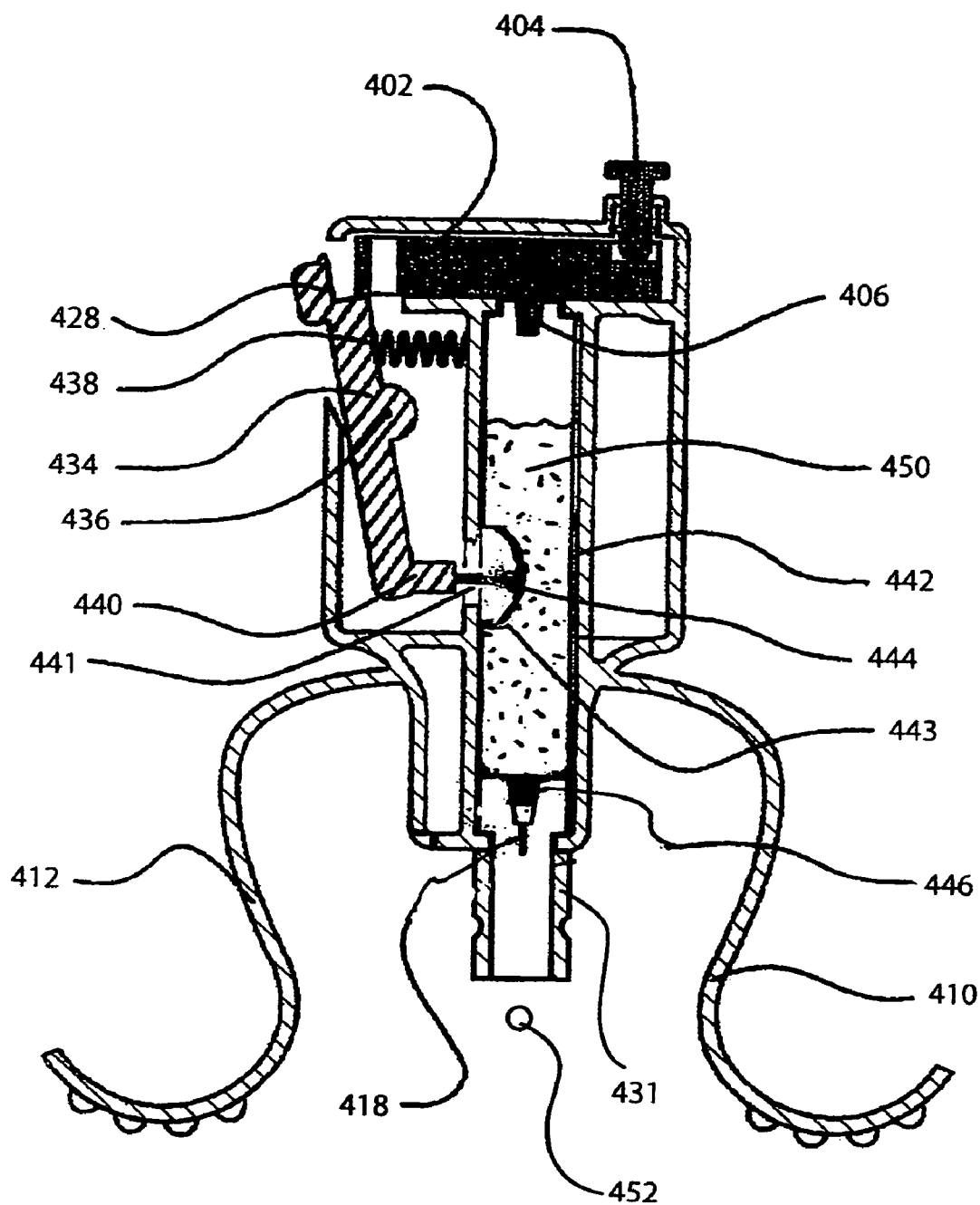
FIG. 34 is a front section view of the third embodiment of the eyedropper of the present invention in the use position.

Cartridge 442 can be seen in section view. The cartridge 442 is elongate and in the preferred embodiment cylindrical. The cartridge 442 is capped on top by top cover that includes an air intake check valve. Cartridge 442 terminates at its bottom in tubular exit aperture 418. A removable cone shaped cap 419 protects aperture 418 and lower cylindrical portion 431 from dirt during non-use. An outwardly directed check valve 446 is mounted just before exit aperture 418. A resilient membrane 444 is fixed over an aperture 443 located in the side wall of cartridge 442. L shaped arm 434 pivots about post 436 and is spring biased 438 to push the bottom portion 440 of L shaped arm 434 into the resilient membrane 444. The thread tip portion 441 of bottom portion 40 is screw threaded into bottom portion 440 thereby allowing the user to adjust the distance between the tip 441 and the membrane 444. As the liquid 450 inside the cartridge 442 decreases in volume, the amount of drops dispensed per use out of aperture 418 can decrease because the remaining air inside cartridge 442 is more compressible than the liquid 450. Therefore the user can adjust the tip 441 by turning it counter clockwise to shorten the distance between the tip 441 and the membrane 444 causing the tip 441 to impinge more deeply into membrane 444 and forcing more drops to dispense per usage. The L shaped arm 434 is held in its potential position by a hook 430, shown in FIG. 36 that engages a mating hook 432, also shown in FIG. 36, on the end of L shaped arm 434. When the user pushes button portion 404, it releases the L shaped arm 434 causing tip 441 to push into resilient membrane 444 as shown in FIG. 33. The resulting deformation of membrane 444 causes air pressure to bear down on solution 450 causing a precise amount of solution to be expelled 452 from aperture 418. Aperture 418 is a narrow diameter such as twenty-six gauge tubing, so that after drop 452 is expelled as shown in FIG. 34, no remaining liquid is left on the tip of aperture 418. Lower cylindrical portion 431 surrounds tip 418 so that the user can not have direct access to it thereby preventing accidental pricking of the finger of the user. When a user pushes on button 428 the membrane 44 returns to its original shape as shown in FIG. 33. This return to flat shape causes a small vacuum to occur in the air portion above liquid 450. This vacuum causes additional air to be drawn into check valve 406 thereby re-pressurizing the air portion above liquid 450.

Figure 35:
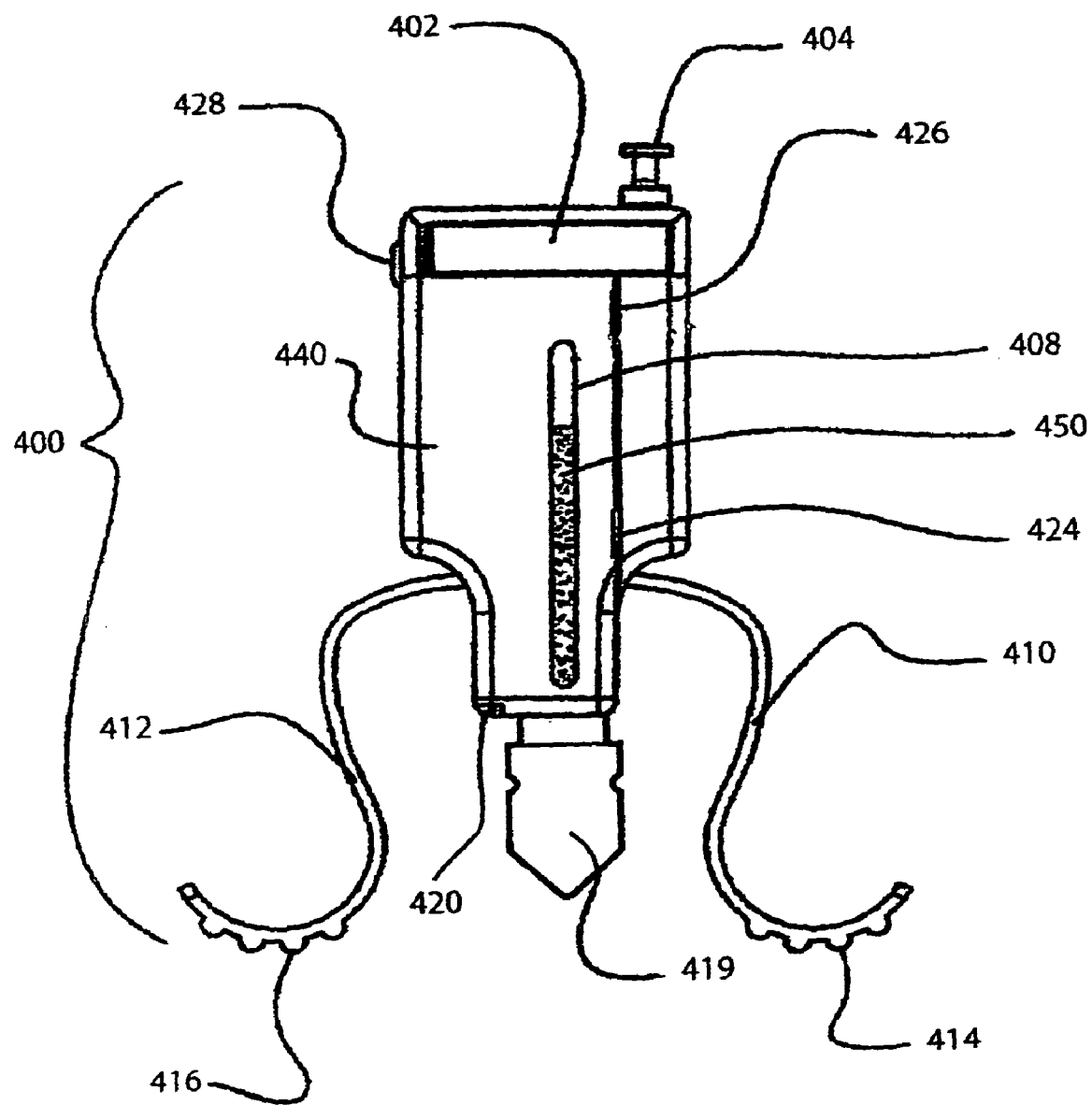
FIG. 35 is a front view of the third embodiment of the eyedropper of the present invention.

FIG. 35 shows a front view of the third embodiment of the invention 400. Hinge 424 allows front door 440 to swing open to replace cartridge 442. Latch member 420 holds the door shut after the cartridge 442 has been installed.

Figure 36:
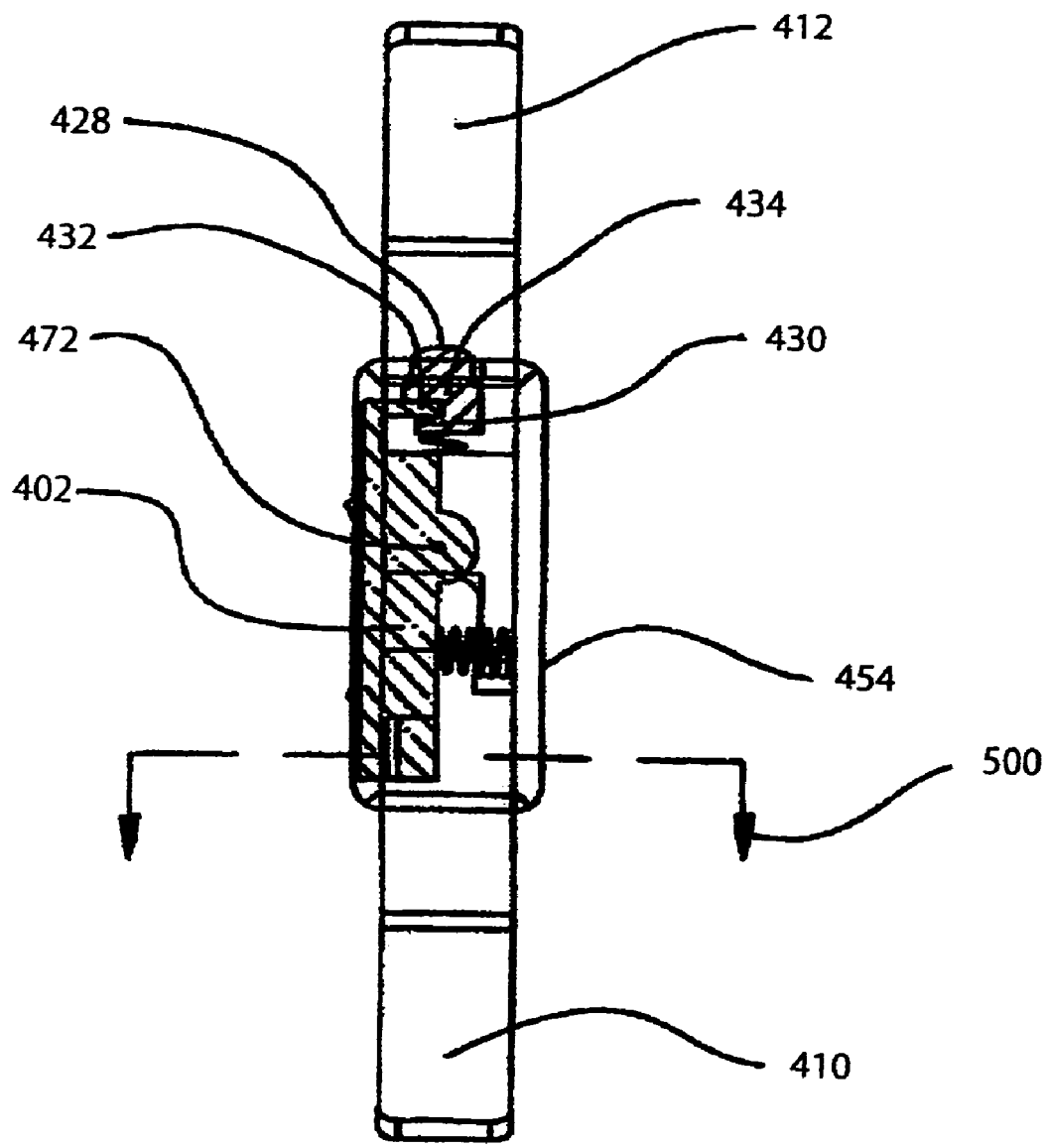
FIG. 36 is a top section view of the third embodiment of the eyedropper of the present invention.

FIG. 36 shows a top section view as defined by section line 470 in FIG. 33. This view clearly shows spring biased activation arm 402. By pushing down on button 404, arm 402 pivots about shaft 472 causing tab 432 to release tab 430 on L shaped arm 434. The angled termination point of tab 430 allows the L shaped arm 434 to be pushed back to its resting place when button 428 is pushed.

FIG. 37 is a top view of the third embodiment 400 of the invention. Push button 404 can be clearly seen. Section view 490 helps further describe the invention as shown in the section view drawing shown in FIG. 33.

Figure 38:
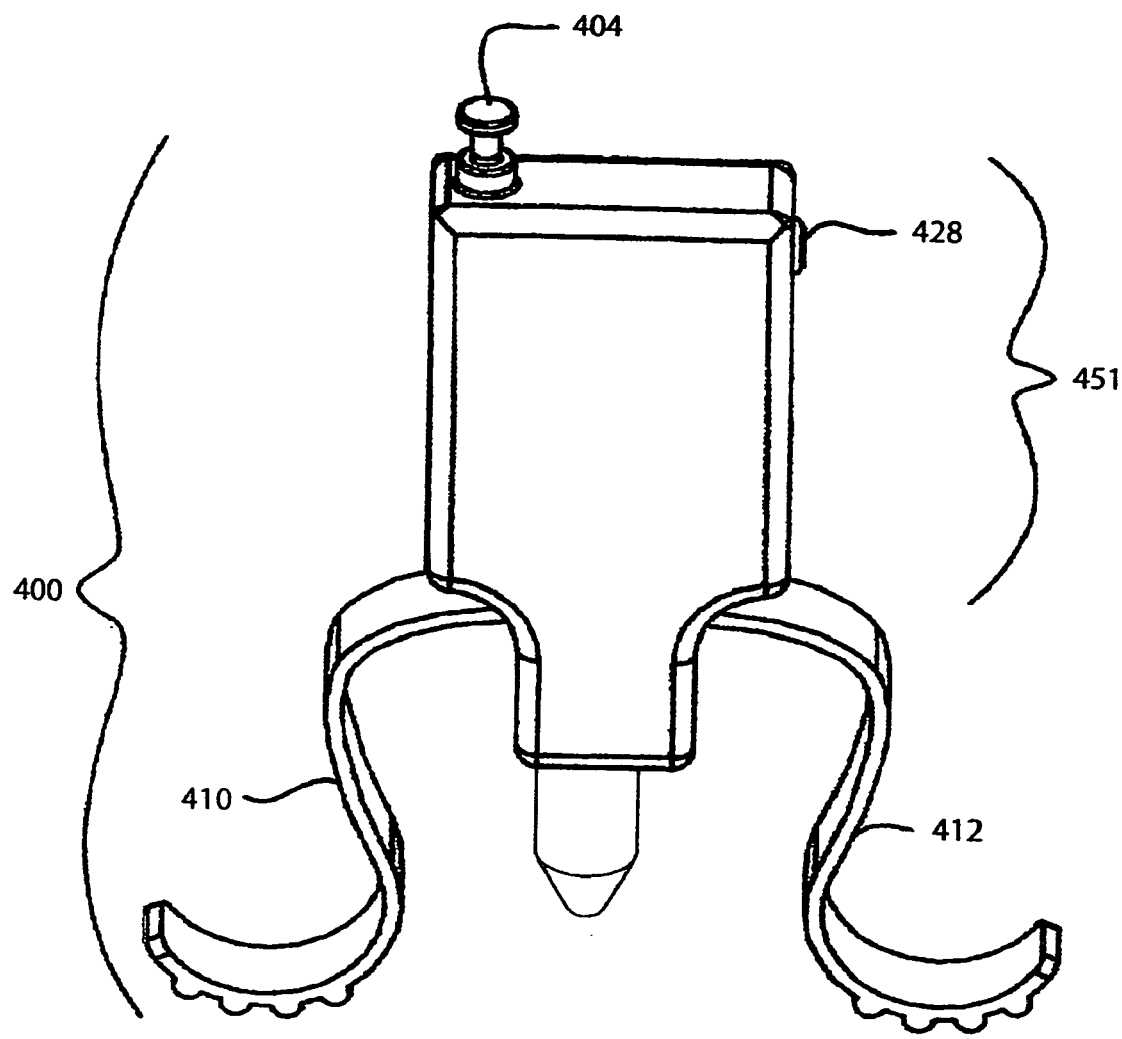
FIG. 38 is a front perspective view of the third embodiment of the eyedropper of the present invention.

FIG. 38 is a front perspective view of the third embodiment 400 of the invention.

Figure 39:
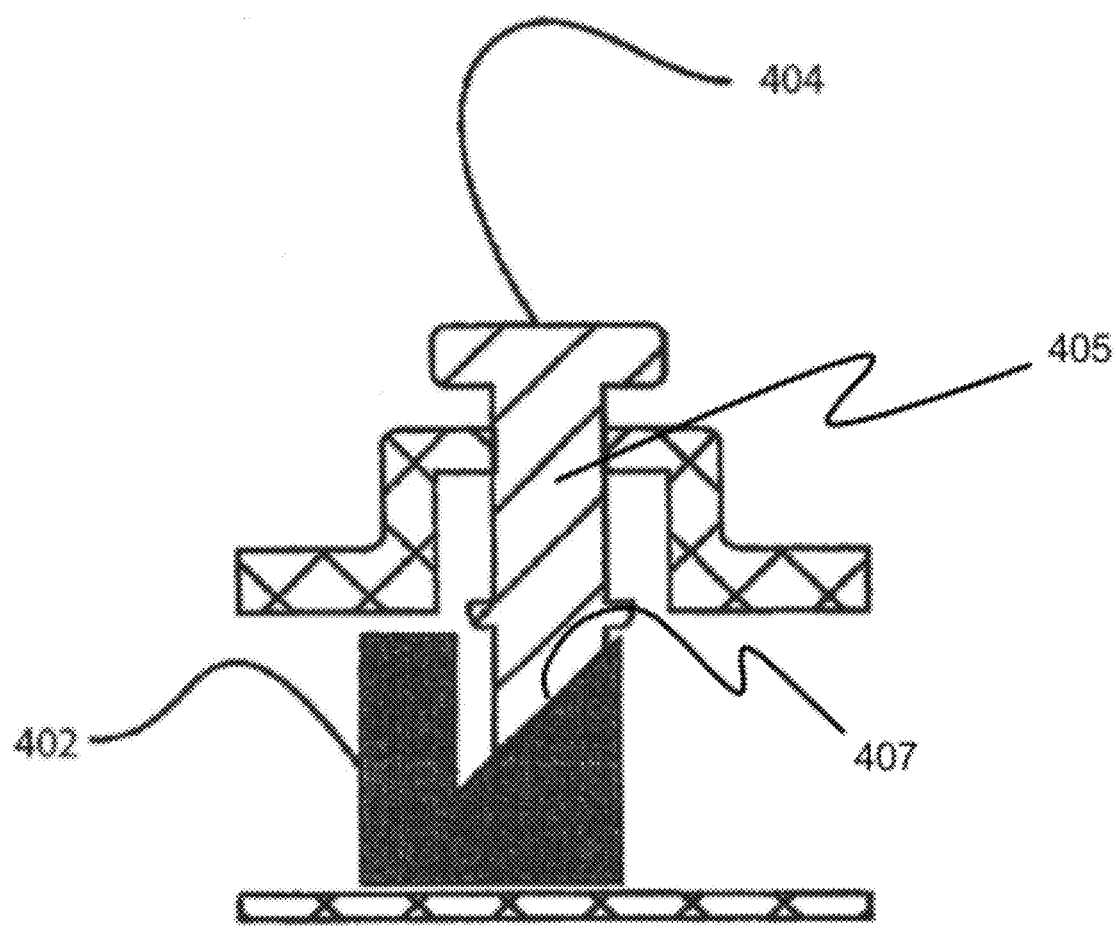
FIG. 39 is a partial section view of the third embodiment of the eyedropper of the present invention showing the trigger release assembly.

FIG. 39 shows a partial section view of the top push button 404 as defined by section line 600 shown in FIG. 36, and its relationship with activation arm 402. In the armed position, push button 404 and its attached post 405 slidably engage activation arm 402 at the top edge of a V shape 407 in activation arm 402. When the user pushes down with one finger onto push button 404, the arm 402 is caused to move to the right. This movement releases the e L shaped arm 434 causing a drop of solution to exit from the discharge orifice 418.

It should also be noted that another version of the present invention can be modified to act as a sterile nose drop applicator. In this version, the flexible downwardly facing legs shown in the above designs would be eliminated. In the nose drop version, a piston would push down on an ampoule similar to that shown in FIGS. 27 and 28 thereby dispensing a precise amount of nose drop solution into the user's nostril.

While the invention has been described in connection with a plurality of embodiments, it is not intended to limit the scope of the invention to the particular form set forth, but on the contrary, it is intended to cover such alternatives, modifications, and equivalents as may be included within the spirit and scope of the invention as defined by the appended claims. Furthermore, elements from one described embodiment can be included in the other described embodiments.

I claim:

1. A precision lid retracting eyedropper device comprising:
a hollow housing;
said housing having an aperture at a first surface thereof and a hollow cylindrical portion at a second surface thereof;
a pair of resilient legs integrally attached to the second surface of said hollow housing;
said legs terminating opposing J shaped feet;
a plurality of friction inducing strips attached to said J shaped feet;
said legs spaced sufficiently apart to allow a user to place one said J foot on the upper portion of the orbital ridge near the eyebrow and the other J foot on the lower portion of the orbital ridge near the cheek bone;
so that when said legs are squeezed together, then said J shaped feet are rested on said upper and lower portions of the orbital ridge, and then said legs are released, the eyelids of the user are forced to remain open because of an outward spring action of said legs;
an eye drop solution storage chamber located within said hollow housing;
a pump assembly located within said hollow housing;
said pump assembly comprising a resilient tubular member having an inwardly directed check valve positioned in a first end thereof and an outwardly directed check valve positioned in a second end thereof;
an elongate piston member having a first end impinging on a central portion of said resilient tubular member and a second end exiting said housing through the aperture in the first surface thereof where the piston member terminates in a push button;
said solution storage chamber connected to said inwardly directed check valve by a first tubular member;
said outwardly directed check valve of said pump assembly connected by a second tubular member to an exit aperture;
said second tubular member held in place by said hollow cylindrical portion of said housing;
so that when said user presses on said push button, said piston impinges on said resilient tubular member of said pump assembly and forces a precise amount of eye drop solution out of said outwardly directed check valve and out said exit aperture and into said user's eye.

2. A precision lid retracting eyedropper device as claimed in claim 1 wherein said elongate piston member is oriented and moves along an axis extending from said push button to said exit aperture and said pump assembly is oriented orthogonal to said piston allowing said piston to be at right angles to and to directly impinge upon the central portion of said tubular member of said pump assembly.

3. A precision lid retracting eyedropper device as claimed in claim 1 wherein said solution storage chamber is constructed of resilient material allowing said chamber to collapse as solution is withdrawn therefrom so that no air can be found in said solution chamber.

4. A precision lid retracting eyedropper device as claimed in claim 1 wherein said push button includes a counting mechanism and a window that displays advancing numbers, so that each time said button is pushed, the said counting mechanism advances by one digit.

5. A precision lid retracting eyedropper device as claimed in claim 1 wherein said exit aperture consists of eighteen gauge or smaller tubing to decrease the chance of residual drops remaining on said aperture after each use.

* * * * *